(12) United States Patent
James et al.

(10) Patent No.: US 12,186,411 B2
(45) Date of Patent: *Jan. 7, 2025

(54) LABELED PROBE AND METHODS OF USE

(71) Applicant: The Board of Trustees of the Leland Stanford Junior University, Stanford, CA (US)

(72) Inventors: Michelle L. James, Menlo Park, CA (US); Katrin I. Andreasson, Stanford, CA (US)

(73) Assignee: The Board of Trustees of Leland Stanford Junior University, Stanford, CA (US)

(*) Notice: Subject to any disclaimer, the term of this patent is extended or adjusted under 35 U.S.C. 154(b) by 205 days.

This patent is subject to a terminal disclaimer.

(21) Appl. No.: 17/521,974

(22) Filed: Nov. 9, 2021

(65) Prior Publication Data

US 2022/0062449 A1 Mar. 3, 2022

Related U.S. Application Data

(62) Division of application No. 15/775,450, filed as application No. PCT/US2016/061577 on Nov. 11, 2016, now Pat. No. 11,213,598.

(60) Provisional application No. 62/254,396, filed on Nov. 12, 2015.

(51) Int. Cl.
*A61K 51/10* (2006.01)
*C07K 16/28* (2006.01)

(52) U.S. Cl.
CPC ...... *A61K 51/1027* (2013.01); *A61K 51/1093* (2013.01); *C07K 16/2803* (2013.01)

(58) Field of Classification Search
CPC ............ A61K 51/1027; A61K 51/1093; C07K 16/2803
USPC .......... 424/1.11, 1.49, 1.65, 1.69, 1.81, 1.85, 424/1.89, 9.1, 9.2
See application file for complete search history.

(56) References Cited

U.S. PATENT DOCUMENTS 11,213,598 B2 * 1/2022 James ................ A61K 51/1027

OTHER PUBLICATIONS

Arbit, Enud, et al., "Quantitative studies of monoclonal antibody targeting to disialoganglioside Go2 in human brain tumors," European Journal of Nuclear Medicine, 1995, pp. 419-426, vol. 22, No. 5.
Blankenberg, Francis G., "Imaging the Molecular Signatures of Apoptosis and Injury with Radiolabeled Annexin V," Proceedings of the American Thoracic Society, 2009, pp. 469-476, vol. 6, doi: 10.1513/pats.200901-001AW.
Boutin, Hervé, et al., "18F-GE-180: a novel TSPO radiotracer compared to 11C-R-PK11195 in a preclinical model of stroke," European Journal of Nuclear Medicine and Molecular Imaging, 2015, pp. 503-511, vol. 42, doi: 10.1007/s00259-014-2939-8.
Chen, Li C., et al., "Regulation of TREM Expression in Hepatic Macrophages and Endothelial Cells during Acute Endotoxemia," Experimental and Molecular Pathology, 2008, pp. 145-155, vol. 84, No. 2, doi: 10.1016/j.yexmp.2007.11.004.
Chen, Ming-Kai and Tomás R. Guilarte, "Translocator Protein 18kDA (TSPO): Molecular Sensor of Brain Injury & Repair," Pharmacology & Therapeutics, 2008, pp. 1-17, vol. 118, No. 1, doi: 10.1016/j.pharmthera.2007.12.004.
Collins, C E, et al., "Elevated synovial expression of triggering receptor expressed on myeloid cells 1 in patients with septic arthritis or rheumatoid arthritis," Annals of the Rheumatic Diseases, 2009, pp. 1768-1774, vol. 68, doi: 10.1136/ard.2008.089557.
Cooper, Maggie S., et al., "Comparison of 64Cu-complexing bifunctional chelators for radioimmunoconjugation: labeling efficiency, specific activity and in vitro/in vivo stability," Bioconjugate Chemistry, 2012, pp. 1029-1039, vol. 23, No. 5, doi: 10.1021/bc300037w.
Gibot, Sébastien, et al., "Plasma Level of a Triggering Receptor Expressed on Myeloid Cells-1: Its Diagnostic Accuracy in Patients with Suspected Sepsis," Annals of Internal Medicine, 2004, pp. 9-15, vol. 141, No. 1.
Gibot, Sébastien and Aurélie Cravoisy, "Soluble Form of the Triggering Receptor Expressed on Myeloid Cells-1 as a Marker of Microbial Infection," Clinical Medicine & Research, 2004, pp. 181-187, vol. 2, No. 3.
Ho, Chao-Chi, et al., "TREM-1 Expression in Tumor-associated Macrophages and Clinical Outcome in Lung Cancer," American Journal of Respiratory and Critical Care Medicine, 2008, pp. 763-770, vol. 177, doi: 10.1164/rccm.200704-6410C.
Ilovich, Ohad, et al., "Development and Validation of an Immuno-PET Tracer as a Companion Diagnostic Agent for Antibody-Drug Conjugate Therapy to Target the CA6 Epitope1," Radiology, 2015, pp. 191-198, vol. 276, No. 1, radiology.rsna.org.
Jacobs, Andreas H., et al., "Noninvasive molecular imaging of neuroinflammation," Journal of Cerebral Blood Flow & Metabolism, 2012, pp. 1393-1415, vol. 32, doi: 10.1038/jcbfm.2012.53.
James, Michelle L., et al., "DPA-714, a New Translocator Protein-Specific Ligand: Synthesis, Radiofluorination, and Pharmacologic Characterization," The Journal of Nuclear Medicine, 2008, pp. 814-822, vol. 49, No. 5, doi: 10.2967/jnumed.107.046151.
James, Michelle L., et al., "PET Imaging of Translocator Protein (18 kDa) in a Mouse Model of Alzheimer's Disease Using N-(2,5-Dimethoxybenzyl)-2-18F-Fluoro-N-(2-Phenoxyphenyl)Acetamide," The Journal of Nuclear Medicine, 2015, pp. 311-316, vol. 56, No. 2, doi: 10.2967/jnumed.114.141648.
Johansson, Jenny U., et al., "Prostaglandin signaling suppresses beneficial microglial function in Alzheimer's disease models," The Journal of Clinical Investigation, 2015, pp. 350-364, vol. 125, No. 1, doi: 10.1172/JCI77487.

(Continued)

*Primary Examiner* — Micah Paul Young
(74) *Attorney, Agent, or Firm* — Thomas| Horstemeyer, LLP

(57) ABSTRACT

The present disclosure provides for methods and compositions useful for imaging inflammation and inflammatory disease markers with an affinity for TREM-1 antibodies. The methods and compositions can include a labeled probe having a TREM-1 antibody and a radiolabel.

12 Claims, 11 Drawing Sheets

(56) References Cited

OTHER PUBLICATIONS

Klohs, Jan, et al., "In Vivo Imaging of the Inflammatory Receptor CD40 After Cerebral Ischemia Using a Fluorescent Antibody," Stroke, 2008, pp. 2845-2852, doi: 10.1161/STROKEAHA.107. 509844.

Knapp, Sylvia, et al., "Cutting Edge: Expression Patterns of Surface and Soluble Triggering Receptor Expressed on Myeloid Cells-1 in Human Endotoxemia1," The Journal of Immunology, 2004, pp. 7131-7134, vol. 173, The American Association of Immunologists, Inc., doi: 10.4049/jimmunol.173.12.7131.

Knowles, Scott M. and Anna M. Wu, "Advances in Immuno-Positron Emission Tomography: Antibodies for Molecular Imaging in Oncology," Journal of Clinical Oncology, 2012, pp. 3884-3892, vol. 30, No. 31, doi: 10.1200/JCO.2012.42.4887.

Konishi, Shota, et al., "Determination of Immunoreactive Fraction of Radiolabeled Monoclonal Antibodies: What Is an Appropriate Method?," Cancer Biotherapy & Radiopharmaceuticals, 2004, pp. 706-715, vol. 19, No. 6.

Krueger, Martin, et al., "Blood-brain barrier breakdown involves four distinct stages of vascular damage in various models of experimental focal cerebral ischemia," Journal of Cerebral Blood Flow & Metabolism, 2015, pp. 292-303, vol. 35, doi: 10.1038/jcbfm.2014.199.

Lagler, Heimo, et al., "TREM-1 Activation Alters the Dynamics of Pulmonary IRAK-M Expression In Vivo and Improves Host Defense during Pneumococcal Pneumonia1," The Journal of Immunology, 2009, pp. 2027-2036, vol. 183, The American Association of Immunologists, Inc., doi: 10.4049/jimmunol.0803862.

Lartey, Frederick M., et al., "PET Imaging of Stroke-Induced Neuroinflammation in Mice Using [18F]PBR06," Molecular Imaging and Biology, 2014, pp. 109-117, vol. 16, No. 1, doi: 10.1007/s11307-013-0664-5.

Li, Jun, et al., "Misoprostol, an anti-ulcer agent and PGE2 receptor agonist, protects against cerebral ischemia," Neuroscience Letters, 2008, pp. 210-215, vol. 438, No. 2, doi: 10.1016/j.neulet.2008.04.054.

Liang, Xibin, et al., "Signaling via the prostaglandin E2 receptor EP4 exerts neuronal and vascular protection in a mouse model of cerebral ischemia," The Journal of Clinical Investigation, 2011, pp. 4362-4371, vol. 121, No. 11, doi: 10.1172/JCI46279.

Liu, Christina H., et al., "Forebrain Ischemia-Reperfusion Simulating Cardiac Arrest in Mice Induces Edema and DNA Fragmentation in the Brain," Molecular Imaging, 2007, pp. 156-170, vol. 6, No. 3.

Luus, Christopher, et al., "The development of PET radioligands for imaging the translocator protein (18 kDa): What have we learned?," Journal of Labelled Compounds and Radiopharmaceuticals, 2010, pp. 501-510, vol. 53, doi: 10.1002/jlcr.1752.

Lyman, Monty, et al., "Neuroinflammation: The role and consequences," Neuroscience Research, 2014, pp. 1-12, vol. 79, doi: 10.1016/j.neures.2013.10.004.

Martin, Abraham, et al., "In Vivo PET Imaging of the a4B2 Nicotinic Acetylcholine Receptor As a Marker for Brain Inflammation after Cerebral Ischemia," The Journal of Neuroscience, 2015, pp. 5998-6009, vol. 35, No. 15, doi: 10.1523/JNEUROSCI. 3670-14.2015.

McCullough, Louise, et al., "Neuroprotective Function of the PGE2 EP2 Receptor in Cerebral Ischemia," The Journal of Neuroscience, 2004, pp. 257-268, vol. 24, No. 1, doi: 10.1523/JNEUROSCI.4485-03.2004.

Murakmai, Yousuke, et al., "Induction of Triggering Receptor Expressed on Myeloid Cells 1 in Murine Resident Peritoneal Macrophages by Monosodium Urate Monohydrate Crystals," Arthritis & Rheumatism, 2006, pp. 455-462, vol. 54, No. 2, doi: 10.1002/art.21633.

Owen, David R., et al., "An 18-kDa Translocator Protein (TSPO) polymorphism explains differences in binding affinity of the PET radioligand PBR28," Journal of Cerebral Blood Flow & Metabolism, 2012, pp. 1-5, vol. 32, doi: 10.1038/jcbfm.2011.147.

Park, Jae Jun, et al., "Correlation of Serum-Soluble Triggering Receptor Expressed on Myeloid Cells-1 with Clinical Disease Activity in Inflammatory Bowel Disease," Digestive Diseases and Sciences, 2009, pp. 1525-1531, vol. 54, doi: 10.1007/s10620-008-0514-5.

Schenk, Mirjam, et al., "TREM-1-expressing intestinal macrophages crucially amplify chronic inflammation in experimental colitis and inflammatory bowel diseases," The Journal of Clinical Investigation, 2007, pp. 3097-3106, vol. 117, No. 10, doi: 10.1172/JCI30602.

Schilling, Matthais, et al., "Microglial activation precedes and predominates over macrophage infiltration in transient focal cerebral ischemia: a study in green fluorescent protein transgenic bone marrow chimeric mice," Experimental Neurology, 2003, pp. 25-33, vol. 183, doi: 10.1016/S0014-4886(03)00082-7.

Strbian, D., et al., "The Blood-Brain Barrier is Continuously Open for Several Weeks Following Transient Focal Cerebral Ischemia," Neuroscience, 2008, pp. 175-181, vol. 153, Elsevier Ltd., doi: 10.1016/j.neuroscience.2008.02.012.

Van De Watering, Floor C. J., et al., "Zirconium-89 Labeled Antibodies: A New Tool for Molecular Imaging in Cancer Patients," BioMed Research International, 2014, pp. 1-13, Hindawi Publishing Corporation, doi: 10.1155/2014/203601.

Wang, Yu, et al., "[18F]DPA-714 Pet Imaging of AMD3100 Treatment in a Mouse Model of Stroke," Molecular Pharmaceutics, 2014, pp. 3463-3470, vol. 11, ACS Publications, doi: 10.1021/mp500234d.

Weber, Benjamin, et al., "TREM-1 Deficiency Can Attenuate Disease Severity without Affecting Pathogen Clearance," PLoS Pathogens, 2014, pp. 1-17, vol. 10, No. 1, e1003900, doi: 10.1371/journal.ppat.1003900.

Wu, Anna M., "Antibodies and Antimatter: The Resurgence of Immuno-PET," The Journal of Nuclear Medicine, 2009, pp. 2-5, vol. 50, No. 1, doi: 10.2967/jnumed.108.056887.

Wyss-Coray, Tony and Lennart Mucke, "Inflammation in Neurodegenerative Disease—A Double-Edged Sword," Neuron, 2002, pp. 419-432, vol. 35.

Yasuda, Takeo, et al., "Increased levels of soluble triggering receptor expressed on myeloid cells-1 in patients with acute pancreatitis*," Critical Care Medicine, 2008, pp. 2048-2053, vol. 36, No. 7, doi: 10.1097/CCM.0b013e31817b8824.

Zeng, Heng, et al., "TREM-1 expression in macrophages is regulated at transcriptional level by NF-jB and PU.1," European Journal of Immunology, 2007, pp. 2300-2308, vol. 37, doi: 10.1002/eji.200737270.

\* cited by examiner

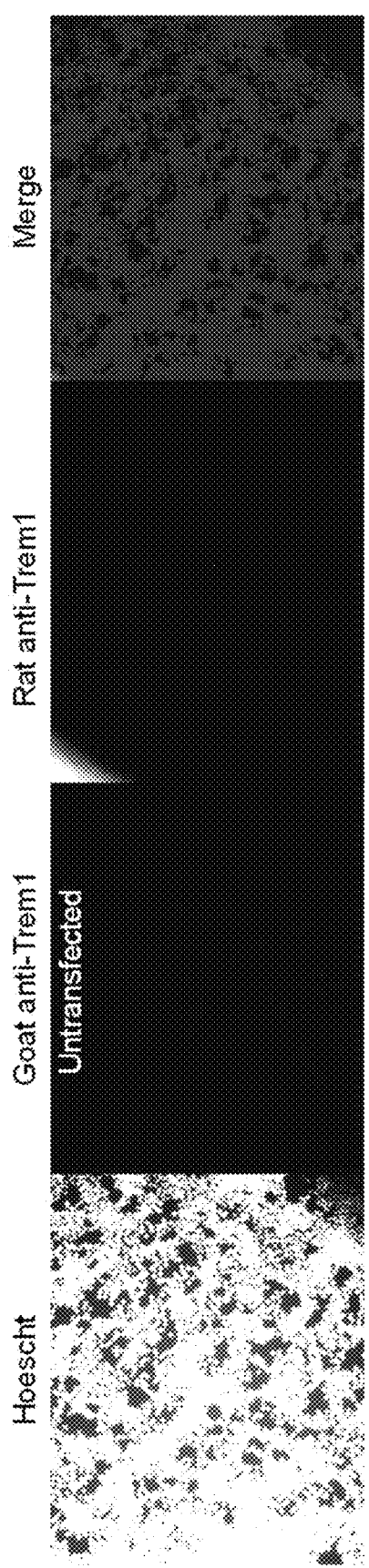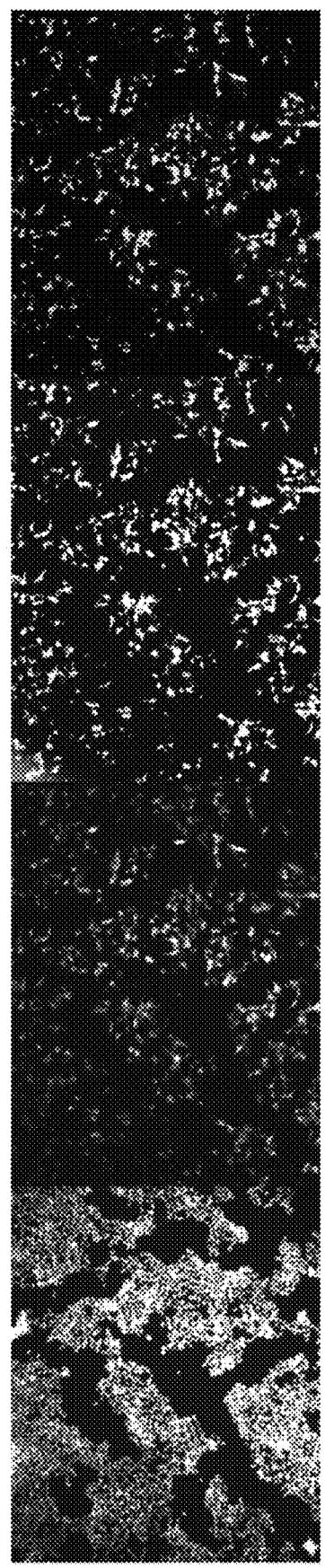

LABELED PROBE AND METHODS OF USE

CROSS-REFERENCE TO RELATED APPLICATIONS

This application is a continuation of U.S. Application having Ser. No. 15/775,450 and filed on May 11, 2018, which application is the 35 U.S.C. § 371 national stage of PCT application having serial number PCT/US2016/061577, filed on Nov. 11, 2016. This application also claims priority to U.S. provisional application entitled "LABELED PROBE AND METHODS OF USE," having Ser. No. 62/254,396 filed on Nov. 12, 2015, each of which are entirely incorporated herein by reference.

BACKGROUND

Molecular imaging using positron emission tomography (PET) has enormous potential for enhancing our understanding of the in vivo role of neuroinflammation, and for enabling longitudinal monitoring of both disease progression and real-time response to novel therapies that directly or indirectly affect immune processes. Neuroinflammation is a key pathological feature of many central nervous system (CNS) diseases. In human neurological disease, our understanding of the temporal dynamics, the anatomical distribution, and the beneficial versus toxic nature of neuroinflammation is currently very limited. Considering that neuroinflammation has become a promising target for developing disease-modifying therapeutics for many of the above listed neurological conditions, our ability to quantify and track the neuroinflammatory component of disease via biomarkers is of great importance. Triggering receptor expressed on myeloid cells (TREM-1) is an inflammatory membrane receptor that is expressed only on myeloid lineage cells and is unique in its function as a potent amplifier of toxic inflammatory responses. TREM-1 aggravates the inflammatory response by synergizing with pattern recognition receptors, such as toll-like receptors (TLRs) and nod-like receptors (NLRs) to amplify pro-inflammatory cytokine production, protease production, and formation of reactive oxygen species (ROS).

Currently the selection of available PET agents for imaging neuroinflammation is limited. Thus, there is a need to develop appropriate imaging agents.

SUMMARY

The present disclosure provides for methods and compositions useful for imaging inflammation and inflammatory disease markers with an affinity for TREM-1 antibodies.

An embodiment of the present disclosure includes a method of imaging an inflammatory disease in a subject, among others, that includes: administering to a subject a labeled probe in a detectably effective amount, wherein the labeled probe includes an agent having an affinity for TREM-1 and a radiolabel, imaging at least a portion of the subject; and detecting the labeled probe, wherein the location of the labeled probe corresponds to inflammation corresponding to the inflammatory disease. In an embodiment, the inflammatory disease is selected from the group consisting of: Alzheimers disease, multiple sclerosis, epilepsy, traumatic brain injury, cancer, arthritis, inflammatory bowel disease, Huntington's disease, ALS, Parkinson's disease, an infectious disease, sepsis, pain, stroke, chronic fatigue syndrome, depression, schizophrenia, and a CNS or peripheral inflammatory disease. In an embodiment, the radiolabel can include: $^{64}Cu$, $^{124}I$, $^{76/77}Br$, $^{86}Y$, $^{89}Zr$, $^{68}Ga$, $^{18}F$, $^{11}C$, $^{125}I$, $^{124}I$, $^{131}I$, $^{123}I$, $^{32}Cl$, $^{33}Cl$, $^{34}Cl$, $^{68}Ga$, $^{74}Br$, $^{76}Br$, $^{76}Br$, $^{77}Br$, $^{78}Br$, $^{86}Zr$, $^{186}Re$, $^{188}Re$, $^{90}Y$, $^{86}Y$, $^{177}Lu$, and $^{153}Sm$. In an embodiment, the radiolabel is conjugated to the agonist antibody of TREM-1 using a chelator such as: (1,4,7,10-tetraazacyclododecane-1,4,7,10-tetraacetic acid); NOTA (1,4,7-Triazacyclononane-1,4,7-triacetic acid); EDTA (Ethylenediaminetetraacetic acid); Df (Desferrioxamine); DTPA (Diethylenetriaminepentaacetic acid; TETA (Triethylenetetramine).

An embodiment of the present disclosure can include a method for diagnosing the presence of an inflammatory disease that includes: administering to a subject a labeled probe in a detectably effective amount, wherein the labeled probe includes an agent having an affinity for TREM-1 and a radiolabel; imaging at least a portion of the subject; and detecting the labeled probe, wherein the location of the labeled probe corresponds to inflammation corresponding to the inflammatory disease, wherein detection of the labeled probe in a location above a threshold is an indication of presence of the inflammatory disease at the location.

An embodiment of the present disclosure can include a method of monitoring the progress of an inflammatory disease in a subject that includes: administering to a subject a labeled probe, wherein the labeled probe includes an agent having an affinity for TREM-1 and a radiolabel; imaging at least a portion of the subject; and detecting the labeled probe, wherein the location of the labeled probe corresponds to inflammation corresponding to the inflammatory disease, wherein the dimensions of the location are monitored over time. In an embodiment, the level of uptake of the labeled probe in a tissue corresponds to the level inflammation in the tissue.

An embodiment of the present disclosure includes a labeled probe including an agent having an affinity for TREM-1 and a radiolabel.

An embodiment of the present disclosure includes a pharmaceutical composition, including: a pharmaceutical carrier and an effective dose of a labeled probe, wherein the labeled probe includes an agent having an affinity for TREM-1 and a radiolabel.

Other compositions, methods, features, and advantages will be or become apparent to one with skill in the art upon examination of the following drawings and detailed description. It is intended that all such additional compositions, methods, features and advantages be included within this description, be within the scope of the present disclosure, and be protected by the accompanying claims.

BRIEF DESCRIPTION OF THE DRAWINGS

Further aspects of the present disclosure will be more readily appreciated upon review of the detailed description of its various embodiments, described below, when taken in conjunction with the accompanying drawings. The components in the drawings are not necessarily to scale, emphasis instead being placed upon clearly illustrating the principles of the present disclosure.

FIGS. 2A-H are fluorescent images of TREM-1 transfection using HEK cells.

FIG. 8A is fluorescent microscopy of TREM1 in HEK293 cells +/−TREM1 transfection. FIG. 8B shows percent binding of tracer (normalized to µg protein) in TREM1 transfected versus untransfected cells.

DETAILED DESCRIPTION

Figure 1:
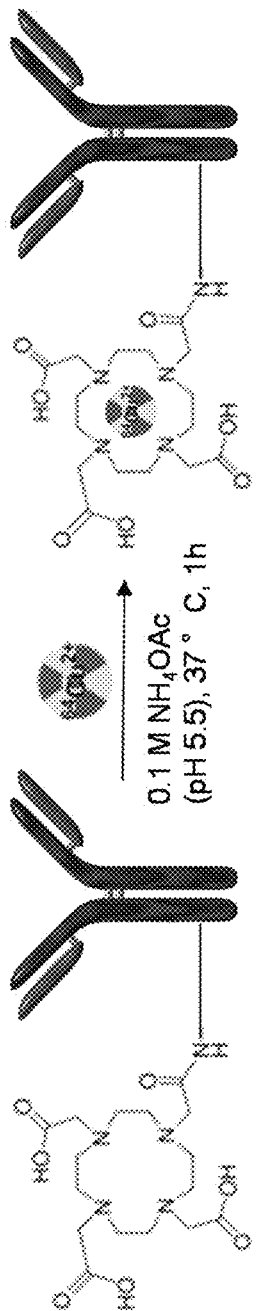
FIG. 1 illustrates the structure of the probe and radiochemistry results.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, synthetic organic chemistry, biochemistry, biology, molecular biology, molecular imaging, and the like, which are within the skill of the art.

The following examples are put forth so as to provide those of ordinary skill in the art with a complete disclosure and description of how to perform the methods and use the probes disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise.

Definitions

In describing and claiming the disclosed subject matter, the following terminology will be used in accordance with the definitions set forth below.

As used herein, "antibody" refers to a protein produced by B cells that is used by the immune system to identify and neutralize foreign compounds, which are also known as antigens. Antibodies are glycoproteins belonging to the immunoglobulin superfamily. Antibodies, recognize and bind to specific epitopes on an antigen.

By "administration" or "administering" is meant introducing a probe or a labeled probe of the present disclosure into a subject. The preferred route of administration of the compounds is intravenous. However, any route of administration, such as oral, topical, subcutaneous, peritoneal, intraarterial, inhalation, vaginal, rectal, nasal, introduction into the cerebrospinal fluid (e.g., intrathecal), or instillation into body compartments can be used.

In accordance with the present disclosure, "a detectably effective amount" of the labeled probe of the present disclosure is defined as an amount sufficient to yield an acceptable image using equipment that is available for clinical use. A detectably effective amount of the labeled probe of the present disclosure may be administered in more than one injection. The detectably effective amount of the labeled probe of the present disclosure can vary according to factors such as the degree of susceptibility of the individual, the age, sex, and weight of the individual, idiosyncratic responses of the individual, and the like. Detectably effective amounts of the probe of the present disclosure can also vary according to instrument and film-related factors. Optimization of such factors is well within the level of skill in the art.

As used herein, the term "subject" includes vertebrates such as humans and mammals (e.g., cats, dogs, horses, etc.).

Typical subjects to which embodiments of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like. Additionally, for in vitro applications, such as in vitro diagnostic and research applications, body fluids and cell samples of the above subjects will be suitable for use, such as mammalian (particularly primate such as human) blood, urine, or tissue samples, or blood, urine, or tissue samples of the animals mentioned for veterinary applications. In some embodiments, a system includes a sample and a subject. The term "living subject" refers to a subject noted above that is alive and is not dead. The term "living subject" refers to the entire subject and not just a part excised (e.g., a liver or other organ) from the living subject.

The term "detectable" refers to the ability to detect a signal over the background signal.

The term "detectable signal" is a signal derived from non-invasive imaging techniques such as, but not limited to, positron emission tomography (PET). The detectable signal is detectable and distinguishable from other background signals that may be generated from the subject. In other words, there is a measurable and statistically significant difference (e.g., a statistically significant difference is enough of a difference to distinguish among the detectable signal and the background, such as about 0.1%, 1%, 3%, 5%, 10%, 15%, 20%, 25%, 30%, or 40% or more difference between the detectable signal and the background) between the detectable signal and the background. Standards and/or calibration curves can be used to determine the relative intensity of the detectable signal and/or the background.

The term "pharmaceutically acceptable carrier" as used herein refers to a diluent, adjuvant, excipient, or vehicle with which a probe of the disclosure is administered and which is approved by a regulatory agency of the Federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable or synthetic origin, such as peanut oil, soybean oil, mineral oil, sesame oil and the like. The pharmaceutical carriers can be saline, gum acacia, gelatin, starch paste, talc, keratin, colloidal silica, urea, and the like. When administered to a patient, the probes of the disclosure and pharmaceutically acceptable carriers preferably should be sterile. Water is a useful carrier when the probe of the disclosure is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol and the like. The present compositions, if desired, can also contain minor amounts of wetting or emulsifying agents, or pH buffering agents. The present compositions advantageously may take the form of solutions, emulsion, sustained-release formulations, or any other form suitable for use.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include the labeled probe, pharmaceutically acceptable salts thereof, with other chemical components, such as physiologically acceptable carriers and excipients. One purpose of a pharmaceutical composition is to facilitate administration of labeled probe to a subject (e.g., human).

Embodiments of the present disclosure may be salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, cam phorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and a specific type of active ingredient (e.g., a labeled probe) in a dosage form may differ depending on various factors. It will be understood, however, that the total daily usage of the compositions of the present disclosure will be decided by the attending physician or other attending professional within the scope of sound medical judgment. The specific effective dose level for any particular subject will depend upon a variety of factors, including for example, the activity of the specific composition employed; the specific composition employed; the age, body weight, general health, sex, and diet of the subject; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

The term "positron emission tomography" as used herein refers to a nuclear medicine imaging technique that produces a three-dimensional image or map of functional/molecular processes in the body. The system detects pairs of gamma rays emitted indirectly by a positron-emitting radioisotope, which is introduced into the body via a molecule specific for a target/process of interest. Images of the target/process of interest in space are then reconstructed by computer analysis. Using statistics collected from tens-of-thousands of coincidence events, a set of simultaneous equations for the total activity of each parcel of tissue can be solved by a number of techniques, and a map of radioactivities as a function of location for parcels or bits of tissue may be constructed and plotted. The resulting map shows the tissues in which the molecular probe has become concentrated. PET technology can be used to trace the biologic pathway of any compound in living humans (and many other species as well), provided it can be radiolabeled with a PET isotope. The half-life of fluorine-18, copper-64, and zirconium-89 are long enough such that imaging agents labeled with these radioisotopes can be manufactured commercially at an off-site location. Other radioisotopes may have shorter half-lives, such as carbon-11 (about 20 min), nitrogen-13 (about 10 min), oxygen-15 (about 2 min), and fluorine-18 (about 110 min).

The term "label" as used herein refers to any moiety that may be linked (e.g. bonded or otherwise associated with) to the agent (e.g., antibody of TREM-1) of the present disclosure and which may be used to provide a detectable image including, but not limited to, a radiolabel such as a PET probe.

The term "in vivo imaging" as used herein refers to methods or processes in which the structural, functional, molecular, or physiological state of a living being is examinable without the need for a life-ending sacrifice.

The term "non-invasive in vivo imaging" as used herein refers to methods or processes in which the structural, functional, molecular, or physiological state of being is examinable by remote physical probing without the need for breaching the physical integrity of the outer (skin) or inner (accessible orifices) surfaces of the body.

Abbreviations

Abbreviations used herein may include: DOTA (1,4,7,10-tetraazacyclododecane-1,4,7,10-tetraacetic acid); NOTA (1,4,7-Triazacyclononane-1,4,7-triacetic acid); EDTA (Ethylenediaminetetraacetic acid); Df (Desferrioxamine); DTPA (Diethylenetriaminepentaacetic acid; TETA (Triethylenetetramine).

General Discussion

Embodiments of the present disclosure provide for labeled probes (e.g., a $^{64}$Cu-DOTA TREM-1 probe), methods of making labeled probes, pharmaceutical compositions including labeled probes, methods of using labeled probes; methods of diagnosing, localizing, monitoring, and/or assessing inflammatory diseases or related biological events using labeled probes; kits for diagnosing, localizing, monitoring, and/or assessing inflammatory diseases or related biological events, and the like. In particular, the present disclosure includes methods relating to non-invasive imaging (e.g., using a positron emission tomography (PET) imaging system) using labeled probes (e.g., a $^{64}$Cu-DOTA TREM-1 probe), in vivo. Additional details are described herein and in the Examples.

Embodiments of the present disclosure provide for the first labeled probe targeting TREM1 for neuroinflammation imaging. Most PET agents currently used to image neuroinflammation were not originally synthesized for that purpose. For example, TSPO tracers were first synthesized in 1984 to investigate the role of the peripheral benzodiazepine receptor in cardiovascular, renal, and cerebral pathologies. The present disclosure used an approach that is unique since it used unbiased transcriptome analyses from studies of neurological disease to identify a promising PET imaging biomarker of neuroinflammation. Since TREM1 is strongly linked to maladaptive microglial responses (generation of pro-inflammatory cytokines and free radicals), as opposed to beneficial functions (e.g., phagocytosis, trophic factor support), this target can serve as an in vivo biomarker of microglial/macrophage functional status. None of the currently available neuroinflammation PET tracers can provide this type of information. In addition, embodiments of the present disclosure provide for a labeled probe that is a neuroinflammatory target that is selectively expressed on myeloid cells.

Embodiments of the present disclosure are advantageous for at least the following reasons. In an embodiment, the labeled probe specifically and selectively binds to TREM-1 in vivo and in vitro. In an embodiment, the sample can be imaged via PET imaging. Embodiments of the present disclosure provide for non-invasive, early detection, staging, and monitoring of inflammatory diseases including but not limited to Alzheimer's disease (AD), sepsis, sepsis induced encephalopathy (SIE), multiple sclerosis, epilepsy, traumatic brain injury, cancer, arthritis, inflammatory bowel diseases (e.g., colitis), Huntington's disease, Amytrophic Lateral Sclerosis (ALS), Parkinson's disease, infectious diseases, pain, stroke, chronic fatigue syndrome, depression, schizophrenia, and a range of other central nervous system and peripheral inflammatory diseases.

Embodiments of the present disclosure include methods for imaging a sample (e.g., tissue or cell(s)) or a subject, that includes contacting a sample with or administering to a subject a labeled probe (e.g., $^{64}$Cu-DOTA TREM-1) and imaging the sample with a PET imaging system. Imaging can be performed in vivo, ex vivo, and/or in vitro. In particular, embodiments of the present disclosure can be used to image inflammatory diseases or related biological events. In this regard, the sample or subject can be tested to determine if the sample or subject includes a inflammatory diseases or related biological conditions, to monitor the progression (or regression) of the inflammatory diseases, or to assess the response of the inflammatory diseases to treatment, to image, and the like. In an embodiment, the tissue or cells can be within a subject or can have been removed from a subject.

In an embodiment, the labeled probe (64Cu-DOTA TREM-1) can be imaged using imaging systems such as a positron emission tomography (PET) imaging systems (and combined PET/CT and PET/MR systems) or an ex vivo/in vitro phosphor imager. In an embodiment, PET imaging is a preferred embodiment. Other types of labeled probes can use appropriate imaging systems.

In an embodiment, the labeled probe can be used in imaging, diagnosing, localizing, monitoring, and/or assessing inflammatory diseases and related biological events as well as tracking response to therapy. For example, embodiments of the present disclosure can be used for imaging, diagnosing, localizing, monitoring, and/or assessing: Alzheimer's disease (AD), multiple sclerosis, epilepsy, traumatic brain injury, cancer, arthritis, inflammatory bowel disease, Huntington's disease, ALS, Parkinson's disease, an infectious disease, sepsis, pain, stroke, chronic fatigue syndrome, depression, schizophrenia, and a CNS or peripheral inflammatory disease. In an embodiment the inflammatory disease can be Alzheimer's disease. In particular, the present disclosure includes methods relating to non-invasive imaging (e.g., using positron emission tomography (PET) imaging system) using the labeled probe in vivo.

TREM-1 is a biomarker of toxic or maladaptive inflammation. TREM-1 is a highly regulated gene tightly associated with microglial maladaptive responses. TREM-1 is expressed in myeloid lineage cells and is a potent amplifier of pro-inflammatory responses. TREM-1 signals through adapter protein DAP12/TYROBP, a critical signaling node that emerged in AD gene-regulatory network analyses. Not only does TREM-1 function in the pathogenesis of AD, but it may also serve as a unique inflammatory marker for maladaptive microglia. Under physiologic conditions, myeloid cells express low levels of TREM-1; however, during pro-inflammatory responses, TREM-1 expression is selectively upregulated in microglia.

The present disclosure describes non-invasive imaging of TREM-1 and its involvement in toxic/maladaptive inflammation in living subjects. In a particular embodiment, a radiolabeled agent (e.g., agonist antibody) for TREM-1 with a PET radioisotope (e.g., copper-64) is provided that can specifically and selectively bind to TREM-1 in vitro in cells transfected with TREM-1 and in vivo in a living subject.

Embodiments of the present disclosure include a labeled probe in a chemical composition, a pharmaceutical composition, or the like. In an embodiment, the labeled probe includes an agent having an affinity for TREM-1 and a radiolabel. In an embodiment, the agent can have an affinity (e.g., a preferential attraction or specific attraction thereto substantially to the exclusion of other proteins and the like associated with inflammatory disease) for TREM-1. In an embodiment, the agent can be a TREM-1 antibody (e.g., humanized or mouse TREM-1 antibody such as one that can be purchased from R&D Systems (e.g., Mouse TREM-1 Antibody, Catalog Number: MAB1187, Human TREM-1 Antibody, Catalog Number: MAB1278), Hycult Biotech, and the like), an engineered fragment of the TREM-1 antibody, a TREM-1 peptide, or a small molecule associated with TREM-1. In an embodiment, the TREM-1 antibody can be a TREM-1 agonist antibody or an antagonist TREM-1 antibody. These monoclonal antibodies (mAbs) have been shown to link directly to the extracellular domain of TREM-1.

In an embodiment, the labeled probe includes on or more radiolabels. In an exemplary embodiment, the radiolabel can include one or more of the following: $^{64}$Cu, $^{124}$I, $^{78/77}$Br, $^{86}$Y, $^{89}$Zr, $^{68}$Ga, $^{18}$F, $^{11}$C, $^{125}$I, $^{124}$I, $^{131}$I, $^{123}$I, $^{32}$Cl, $^{33}$Cl $^{34}$Cl, $^{88}$Ga, $^{74}$Br, $^{78}$Br, $^{78}$Br, $^{77}$Br, $^{78}$Br, $^{89}$Zr, $^{186}$Re, $^{188}$Re, $^{90}$Y, $^{86}$Y, $^{177}$Lu, $^{153}$Sm, $^{14}$C, or $^{3}$H. In an embodiment, the radiolabel can be $^{64}$Cu, $^{124}$I, $^{76/77}$Br, $^{86}$Y, $^{89}$Zr, $^{18}$F, or $^{68}$Ga. In an embodiment, the radiolabel can be $^{64}$Cu.

In an embodiment, the radiolabel can be chelated with the agent using a chelator. In an embodiment, the chelator can have a direct bond to an amino acid or indirect bond (e.g., using a linker) to the agent. For example, the chelator can form a bond to an amino acid of an antibody of TREM-1 such as a lysine group in the antibody or other appropriate group to form a bond. One of skill in the art can select the appropriate bond or linker to be used in a particular situation to retain the properties of the agent, the radiolabel, and the TREM-1 imaging probe. In an embodiment, 1, 2, 3, 4, or 5 radiolabels can be present in the labeled probe. In an embodiment, the radiolabels can be chelated to the sequence using a chelator such as 1, 4, 7, 10-tetraazadodecane-N,N'; N'',N'''-tetraacetic acid (DOTA); 1, 4, 7-triazacyclononane-1, 4, 7-triacetic acid (NOTA); 1,4,8,11-tetraazacyclotetradecane-1, 4, 8, 11-tetraacetic acid (TETA); diethylenetriaminepentaacetic (DTPA), ethylenediaminetetraacetic acid (EDTA), and desferrioxamine (Df), 1,4,7-triazacyclononane-N,N',N''-triacetic acid (NOTA), and derivatives of each of these. In an embodiment, the chelator can be DOTA and optionally bonded via a lysine.

In an embodiment, the $^{64}$Cu-DOTA TREM-1 imaging probe includes a label, $^{64}$Cu, that can be used to detect, image, or otherwise identify the $^{64}$Cu-DOTA TREM-1 probe, quantify the amount of $^{64}$Cu-DOTA TREM-1 probe, determine the location of the $^{64}$Cu-DOTA TREM-1 probe (e.g., in imaging), and combinations thereof. In an embodiment, the chelator for the $^{64}$Cu-DOTA TREM-1 probe is DOTA.

Methods of Use

Embodiments of this disclosure include, but are not limited to: methods of imaging a sample or a subject using the labeled probe (e.g., $^{64}$Cu-DOTA TREM-1 probe); methods of imaging inflammatory disease or related biological conditions using the labeled probe (e.g., $^{64}$Cu-DOTA TREM-1 probe); methods of diagnosing inflammatory disease or related biological conditions using the labeled probe (e.g., $^{64}$Cu-DOTA TREM-1 probe); methods of monitoring the progress of inflammatory disease or related biological conditions using the labeled probe (e.g., $^{64}$Cu-DOTA TREM-1 probe), and the like.

Embodiments of the present disclosure can be used to image, detect, study, monitor, evaluate, assess, and/or screen, inflammatory disease (e.g., Alzheimer's disease, multiple sclerosis, epilepsy, traumatic brain injury, cancer, arthritis, inflammatory bowel disease, Huntington's disease, ALS, Parkinson's disease, an infectious disease, sepsis, pain, stroke, chronic fatigue syndrome, depression, schizophrenia, and a CNS or peripheral inflammatory disease) or related biological conditions in vivo or in vitro using the labeled probe (e.g., $^{64}$Cu-DOTA TREM-1 probe). For example, when the labeled probe is associated with TREM-1, a detectable signal is emitted that is significantly different from the background signal (e.g., non-inflamed areas) above a certain threshold, indicating the presence of inflammatory disease, where the threshold depends upon various variables such as the individual subject, the inflammatory disease, and the like.

In a particular embodiment, the $^{64}$Cu-DOTA TREM-1 probe can be used in imaging Alzheimer's disease. For example, the $^{64}$Cu-DOTA TREM-1 probe is provided or administered to a subject in an amount effective to result in association of the $^{64}$Cu-DOTA TREM-1 probe into TREM-1. The subject is then introduced to an appropriate imaging system (e.g., PET system) for a certain amount of time (e.g., this depends on radioisotope being used). The $^{64}$Cu-DOTA TREM-1 probe becomes associated with TREM-1 and is detected using the imaging system. The location of the detected signal from the $^{64}$Cu-DOTA TREM-1 probe can be correlated with the location of the inflammation associated with the Alzheimer's disease. In an embodiment, the dimensions of the location can be determined as well. Other labeled probes of the present disclosure can be used in a similar manner.

In an embodiment, the steps of this method can be repeated at determined intervals so that the location and/or size/stage of the disease can be monitored as a function of time and/or treatment. In particular, the $^{64}$Cu-DOTA TREM-1 probe can find use in a subject undergoing treatment (e.g., using a drug, etc.), to aid in visualizing the response of the Alzheimer's disease to the treatment. In this embodiment, the $^{64}$Cu-DOTA TREM-1 probe is typically visualized and the imaging signal is quantified prior to treatment, and periodically (e.g., daily, weekly, monthly, intervals in between these, and the like) during treatment, and the like, to monitor the regions and extent of the inflammation. Other labeled probes can be used in a similar manner.

In an embodiment, the method can be used to select appropriate patients to receive therapy. For example, a patient can be given an anti-neuroinflammatory drug, and the inflammation can be measured to determine if the anti-neuroinflammatory drug is having the desired results in the patient.

In an embodiment, the method can be used to design clinical trials of new anti-neuroinflammatory drugs by measuring the change in inflammation in the area of inflammation when administered the new anti-neuroinflammatory drug over the desired time frame.

It should be noted that the amount effective to result in uptake or association of the labeled probe (e.g., $^{64}$Cu-DOTA TREM-1 imaging probe) into the cells or tissue of interest may depend upon a variety of factors, including for example, the age, body weight, general health, sex, and diet of the subject; the time of administration; the route of administration; the rate of excretion of the specific probe employed; the duration of the treatment; the existence of other drugs used in combination or coincidental with the specific composition employed; and like factors, well known in the medical arts.

Kits

The present disclosure also provides packaged compositions or pharmaceutical compositions comprising a pharmaceutically acceptable carrier and a labeled probe (e.g., $^{64}$Cu-DOTA TREM-1 probe) of the disclosure. In certain embodiments, the packaged compositions or pharmaceutical composition includes the reaction precursors to be used to generate the labeled probe according to the present disclosure. Other packaged compositions or pharmaceutical compositions provided by the present disclosure further include materials including at least one of: instructions for using the labeled probe to image a subject, or subject samples (e.g., cells or tissues), which can be used as an indicator of conditions including, but not limited to, inflammatory diseases and biological related conditions.

Embodiments of this disclosure encompass kits that include, but are not limited to, the labeled probe (e.g., $^{64}$Cu-DOTA TREM-1 imaging probe) and directions (written instructions for their use). The components listed above can be tailored to the particular biological condition to be monitored as described herein. The kit can further include appropriate buffers and reagents known in the art for administering various combinations of the components listed above to the subject cell or subject organism. The imaging probe and carrier may be provided in solution or in lyophilized form. When the imaging probe and carrier of the kit are in lyophilized form, the kit may optionally contain a sterile and physiologically acceptable reconstitution medium such as water, saline, buffered saline, and the like.

Dosage Forms

Embodiments of the present disclosure can be included in one or more of the dosage forms mentioned herein. Unit dosage forms of the pharmaceutical compositions (the "composition" includes at least the labeled probe of the present disclosure, e.g., $^{64}$Cu-DOTA TREM-1 imaging probe) of this disclosure may be suitable for oral, mucosal (e.g., nasal, sublingual, vaginal, buccal, or rectal), parenteral (e.g., intramuscular, subcutaneous, intravenous, intra-arterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure typically vary depending on their use. For example, a parenteral dosage form may contain smaller amounts of the active ingredient than an oral dosage form used to treat the same condition or disorder. These and other ways in which specific dosage forms encompassed by this disclosure vary from one another will be readily apparent to those skilled in the art (See, e.g., Remington's Pharmaceutical Sciences, 18th ed., Mack Publishing, Easton, Pa. (1990)).

Typical compositions and dosage forms of the compositions of the disclosure can include one or more excipients. Suitable excipients are well known to those skilled in the art of pharmacy or pharmaceutics, and non-limiting examples of suitable excipients are provided herein. Whether a particular excipient is suitable for incorporation into a composition or dosage form depends on a variety of factors well known in the art including, but not limited to, the way in which the dosage form will be administered to a patient. For example, oral dosage forms, such as tablets or capsules, may contain excipients not suited for use in parenteral dosage forms. The suitability of a particular excipient may also depend on the specific active ingredients in the dosage form. For example, the decomposition of some active ingredients can be accelerated by some excipients, such as lactose, or by exposure to water. Active ingredients that include primary or secondary amines are particularly susceptible to such accelerated decomposition.

The disclosure encompasses compositions and dosage forms of the compositions of the disclosure that can include one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate, or organic acids. An exemplary solubility modulator is tartaric acid.

"Pharmaceutically acceptable salt" refers to those salts that retain the biological effectiveness and properties of the free bases and that are obtained by reaction with inorganic or organic acids such as hydrochloric acid, hydrobromic acid, sulfuric acid, nitric acid, phosphoric acid, methanesulfonic acid, ethanesulfonic acid, p-toluenesulfonic acid, salicylic acid, malic acid, maleic acid, succinic acid, tartaric acid, citric acid, and the like.

Embodiments of the present disclosure include pharmaceutical compositions that include the labeled probe (e.g., $^{64}$Cu-DOTA TREM-1 probe), pharmaceutically acceptable salts thereof, with other chemical components, such as physiologically acceptable carriers and excipients. One purpose of a pharmaceutical composition is to facilitate administration of labeled probe (e.g., $^{64}$Cu-DOTA TREM-1 imaging probe) to a subject (e.g., human).

Embodiments of the present disclosure may be salts and these salts are within the scope of the present disclosure. Reference to a compound of any of the formulas herein is understood to include reference to salts thereof, unless otherwise indicated. The term "salt(s)", as employed herein, denotes acidic and/or basic salts formed with inorganic and/or organic acids and bases. In addition, when an embodiment of the present disclosure contains both a basic moiety and an acidic moiety, zwitterions ("inner salts") may be formed and are included within the term "salt(s)" as used herein. Pharmaceutically acceptable (e.g., non-toxic, physiologically acceptable) salts are preferred, although other salts are also useful, e.g., in isolation or purification steps which may be employed during preparation. Salts of the compounds of an active compound may be formed, for example, by reacting an active compound with an amount of acid or base, such as an equivalent amount, in a medium such as one in which the salt precipitates or in an aqueous medium followed by lyophilization.

Embodiments of the present disclosure that contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, cam phorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Embodiments of the present disclosure that contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine, and the like.

Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the disclosure are also contemplated herein. Solvates of the compounds are preferably hydrates.

The amounts and a specific type of active ingredient (e.g., a labeled probe such as $^{64}$Cu-DOTA TREM-1 probe) in a dosage form may differ depending on various factors. It will be understood, however, that the total daily usage of the compositions of the present disclosure will be decided by the attending physician or other attending professional within the scope of sound medical judgment. The specific effective dose level for any particular subject will depend upon a variety of factors, including for example, the activity of the specific composition employed; the specific composition employed; the age, body weight, general health, sex, and diet of the subject; the time of administration; the route of administration; the rate of excretion of the specific compound employed; the duration of the treatment; the existence of other drugs used in combination or coincidental with the specific composition employed; and like factors well known in the medical arts. For example, it is well within the skill of the art to start doses of the composition at levels lower than those required to achieve the desired effect and to gradually increase the dosage until the desired effect is achieved.

EXAMPLES

Example 1: Radiochemistry

Results of the radiochemistry analyses are shown in FIG. 1.

Methods: DOTA conjugation was performed according to established protocols, using metal-free buffers. After conjugation, matrix-assisted laser desorption/ionization (MALDI) mass spectrometry was conducted to determine the average number of DOTA molecules conjugated per TREM-1 antibody. Subsequently, the DOTA-conjugated TREM-1 mAb was radiolabeled with $^{64}$Cu by incubating it in a [$^{64}$Cu] CuCl$_2$ solution (pH 5.5) at 37° C. for one hour with continual shaking. The reaction was purified via a NAP5 column and specific activity of the final labeled antibody was determined via size exclusion high-performance liquid chromatography (HPLC).

Results: MALDI results showed there are 1.8 DOTA molecules per TREM-1 antibody. [$^{64}$Cu]TREM-1 can be synthesized with high specific radioactivity (>75 GBq/µmol), radiochemical purity (>99%), and labeling efficiency (50-75%), which is sufficient for in vitro and in vivo use.

Example 2: In Vitro Cell Binding

Methods: HEK293 cells were plated in 24-well plates 48 h before transfection w/TREM-1. Untransfected HEK293 cells were used as controls. Some cells were blocked w/TREM-1 antibody 30 min prior to incubation with the [$^{64}$Cu]TREM-1 antibody. All cells were incubated with 5 uCi of [$^{64}$Cu]TREM-1 antibody per well for 1 h or 2 h. Cells were washed with PBS, lysed with RIPA buffer, and the activity counted in a gamma counter. Radioactive counts were normalized to the amount of protein in each well via BCA assay.

Results: FIG. 2 shows that [$^{64}$Cu]TREM-1 displayed >24-fold higher binding in transfected versus untransfected cells (0.0556±0.0018 vs. 0.002±0.0002, p<0.0001, n=4 replicates), verifying in vitro its high specificity for TREM-1. Blocking studies with unlabeled anti-TREM-1 mAb led to a significant reduction of [$^{64}$Cu] TREM-1 binding in transfected cells (0.0556±0.0018 vs. 0.0167±0.0007, p<0.0001, n=4 replicates), further corroborating specificity of this PET imaging probe.

Example 3: In Vivo Imaging Studies

Figure 4:
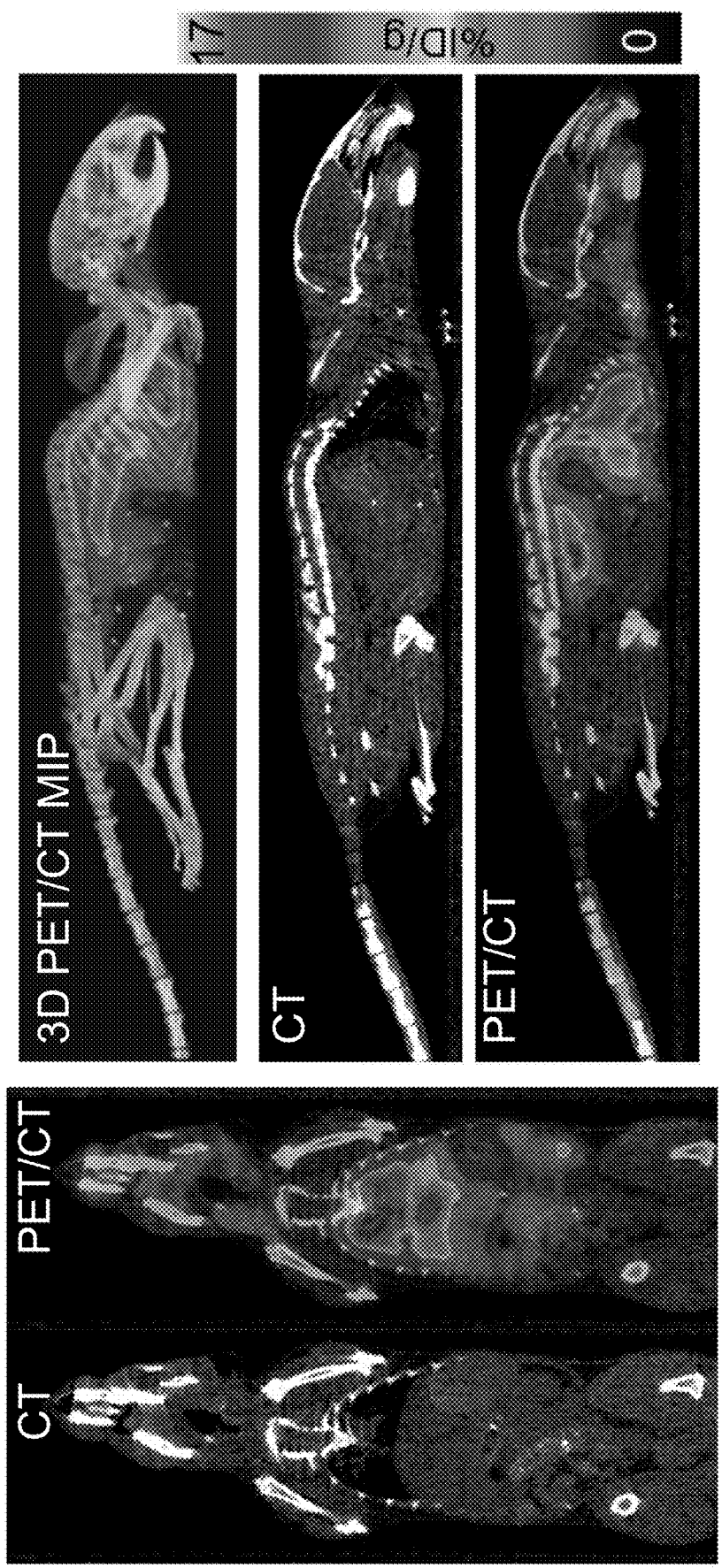
FIG. 4 compares imaging from PET and CT modalities of wild-type mice at 3 hours post-injection of [$^{64}Cu$]TREM-1.
Figure 5:
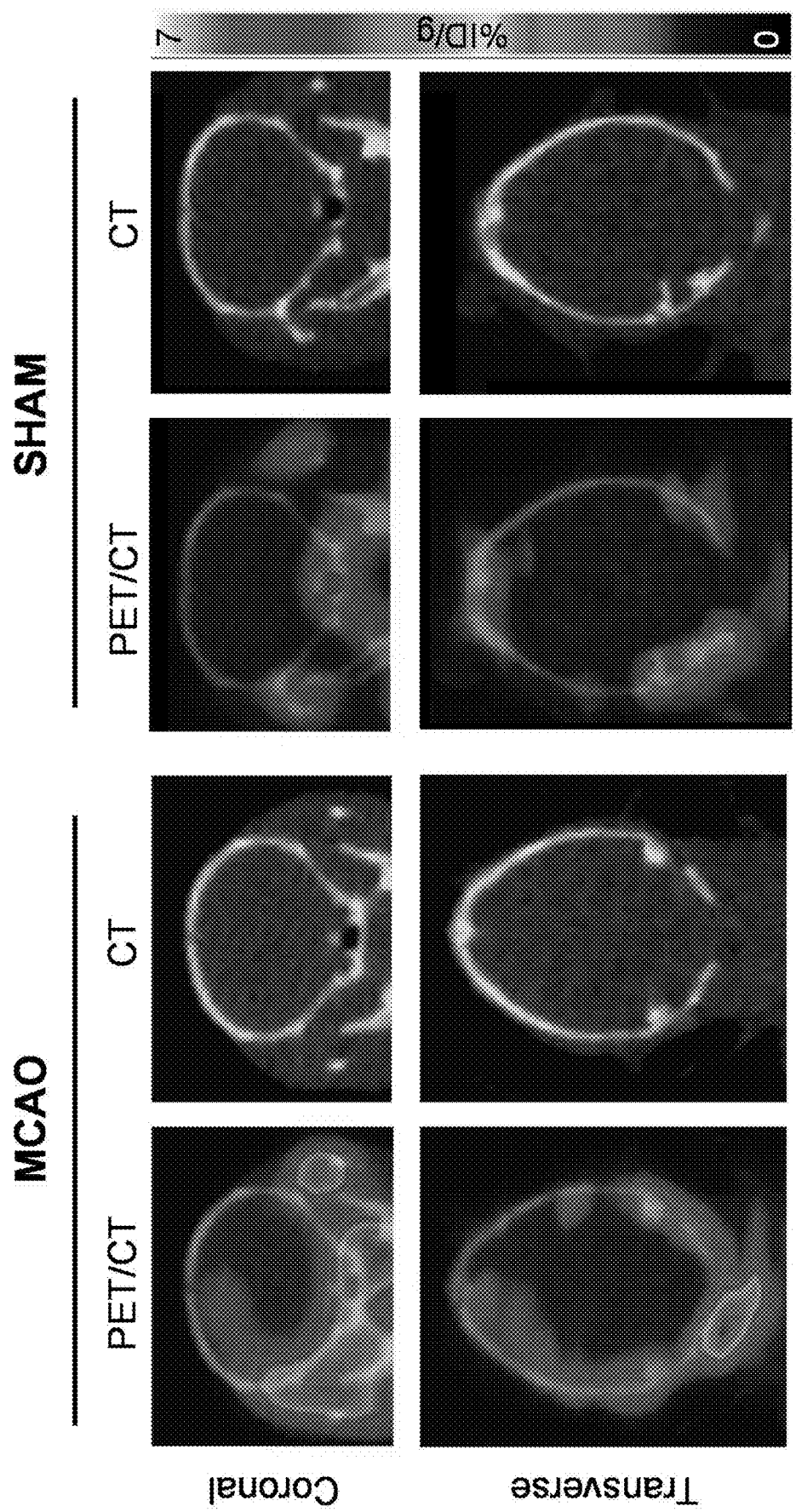
FIG. 5 shows PET and CT images demonstrating visualization of TREM-1 in MCAo stroke vs. sham mice at 19 hours post-injection of [$^{64}$Cu]TREM-1.

Methods: PET/CT imaging of middle cerebral artery occlusion (MCAo) mice was performed to investigate the feasibility of using [$^{64}$Cu]TREM-1 to visualize neuroinflammation in vivo. We selected the MCAo model of cerebral ischemia since the time-course of macrophage infiltration and microglial activation in the brain infarct is well documented, and because this model is commonly used to evaluate candidate microglial-PET tracers. B6 mice (n=3), MCAo (n=9), and sham (n=9) mice were injected via tail vein with 80-85 µCi of [$^{64}$Cu]TREM-1 in a saline solution (0.9% sodium chloride) and imaged using PET/CT at 3 h post-injection (FIG. 4). They were imaged again at 19 h post-injection, which was 1.5-2 days after surgery/stroke (FIG. 5).

Figure 6:
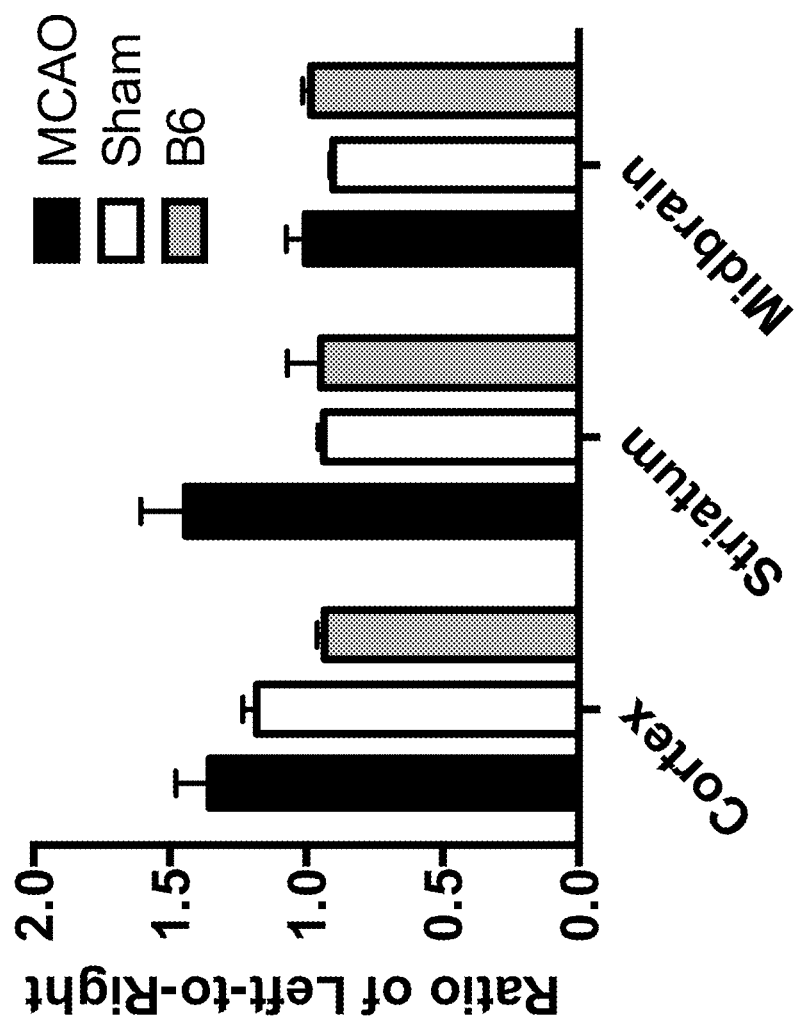
FIG. 6 shows the quantitation of [$^{64}$Cu]TREM-1 PET signal in brain regions from each hemisphere of MCAo stroke versus sham mice at 19 hours post-injection.
Figure 7:
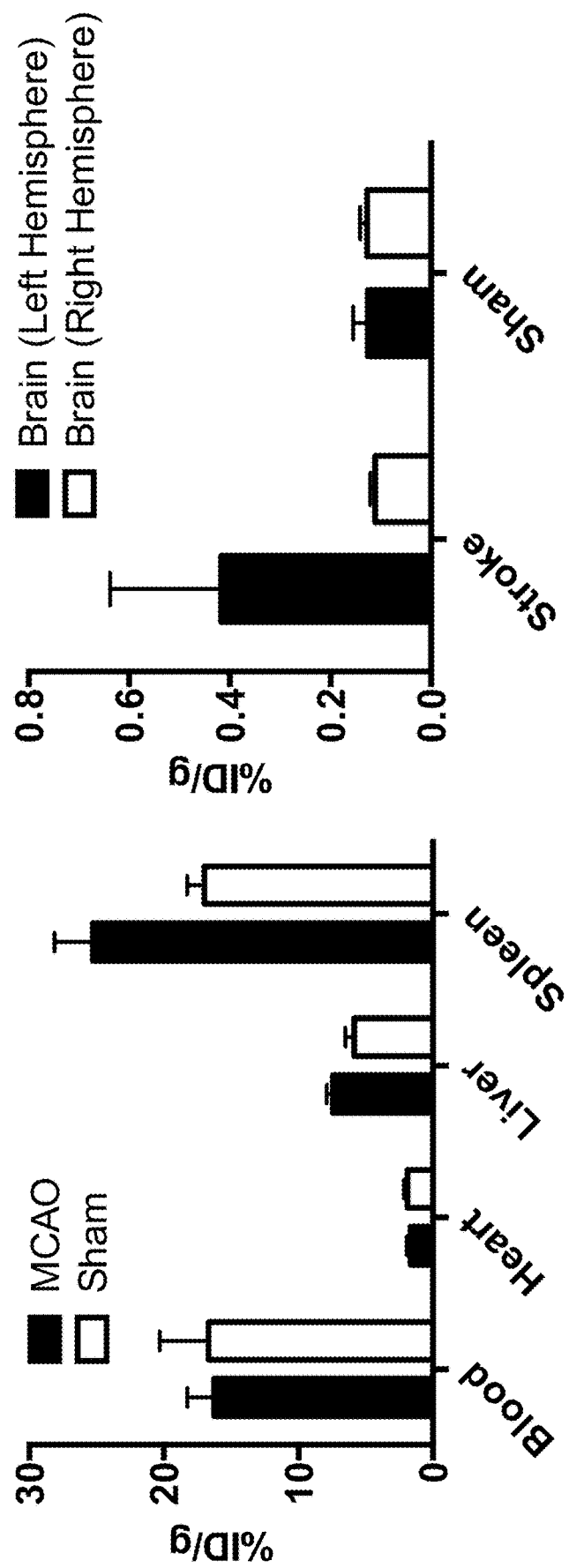
FIG. 7 shows ex vivo biodistribution of [$^{64}$Cu]TREM-1 in organs from MCAo and sham mice 19 hours post-injection of tracer (and 2 days after stroke surgery).
Figure 8A:
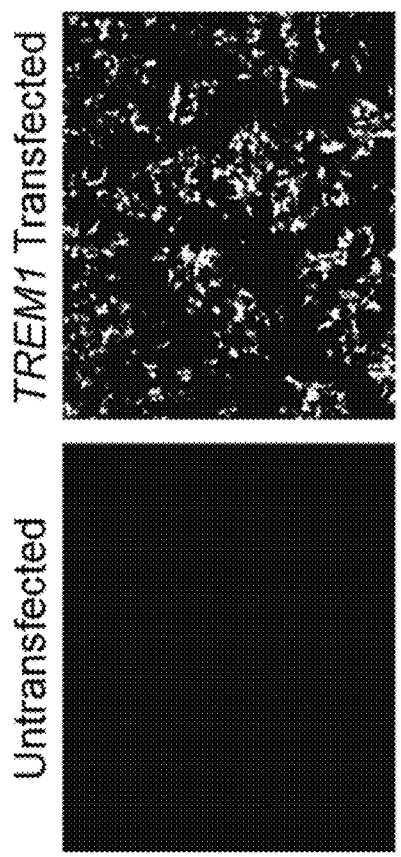
FIGS. 8A-B demonstrate [$^{64}$Cu]TREM1-mAb PET tracer binds to TREM1 in vitro with high specificity.
Figure 8B:
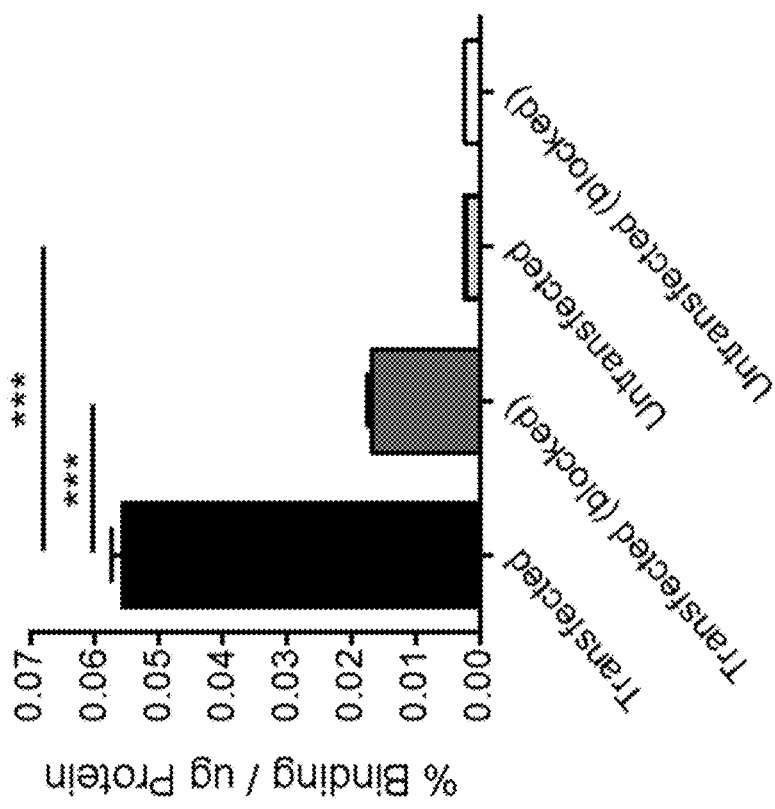
Figure 9:
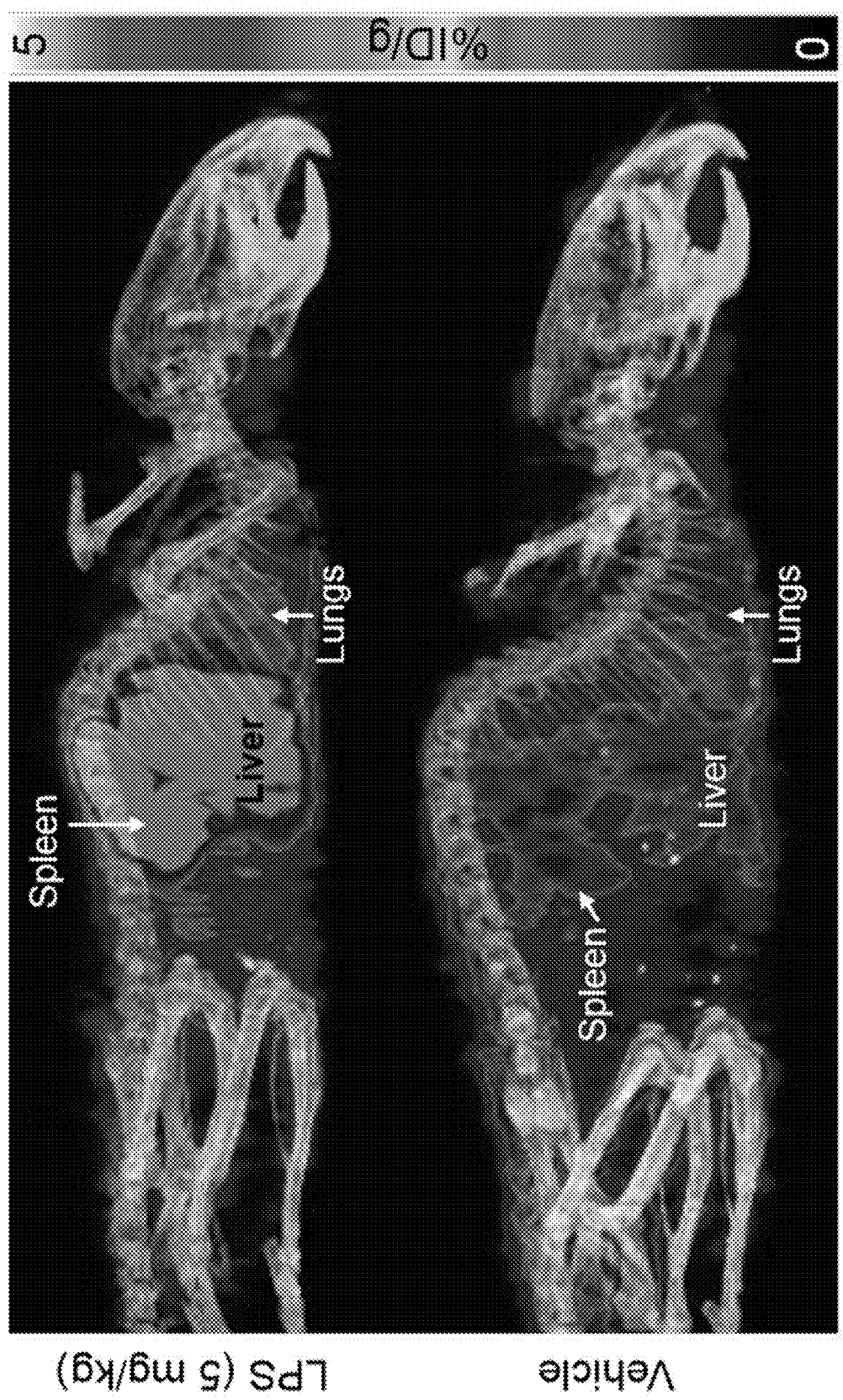
FIG. 9 is in vivo PET imaging of LPS-induced sepsis using [$^{64}$Cu]TREM1-mAb. Images were acquired 24 h after i.p. injection of LPS or vehicle, and are displayed as a maximum intensity projection.
Figure 10:
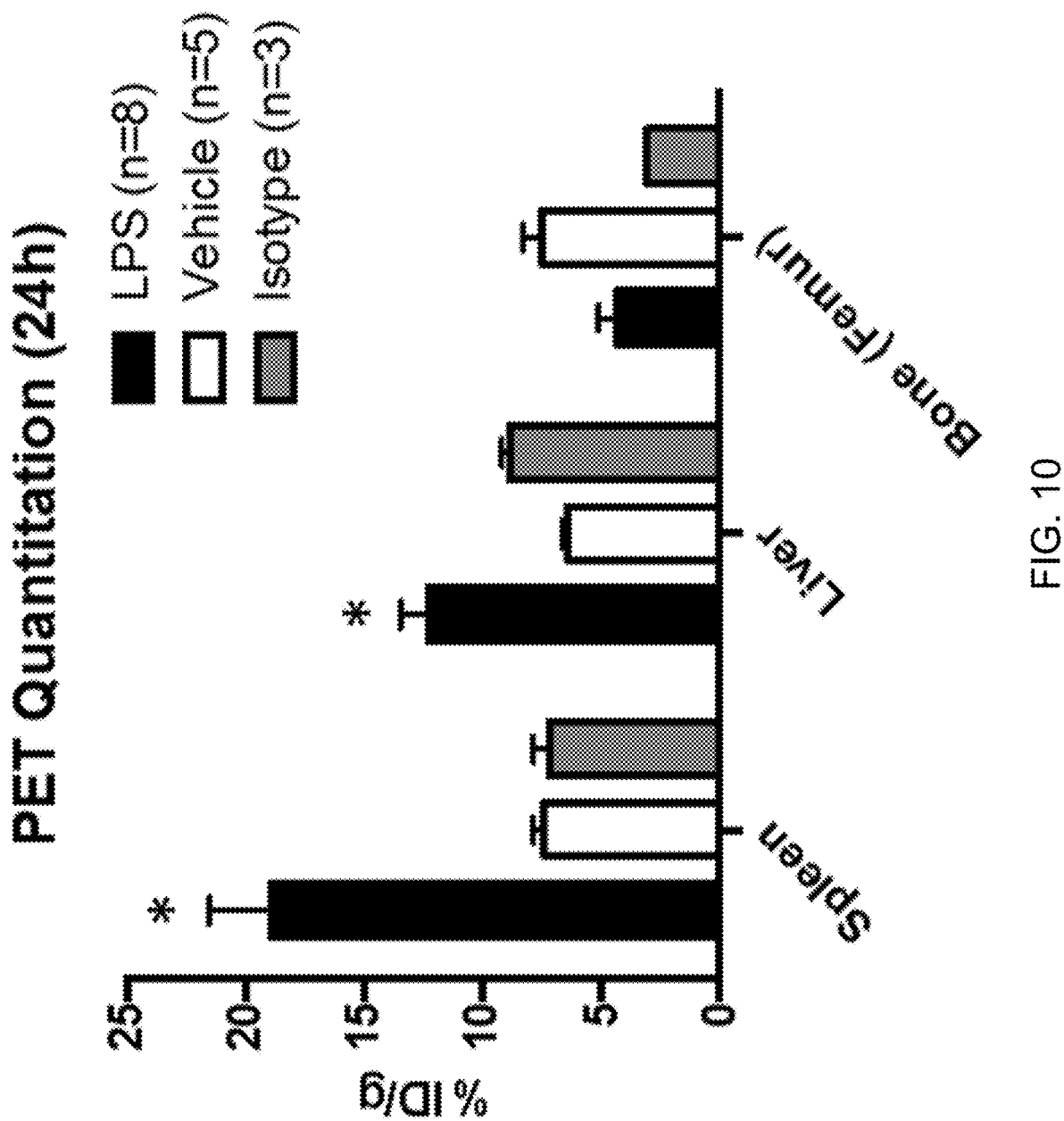
FIG. 10 demonstrates significantly higher uptake of [$^{64}$Cu]TREM1-mAb in spleen and liver of mice 24 h post injection of LPS compared to vehicle treated mice and LPS mice injected with radiolabeled isotope control. Results are from in vivo PET quantification 24 h after mice received i.p. injection of LPS (5 mg/kg) or saline alone.
Figure 11:
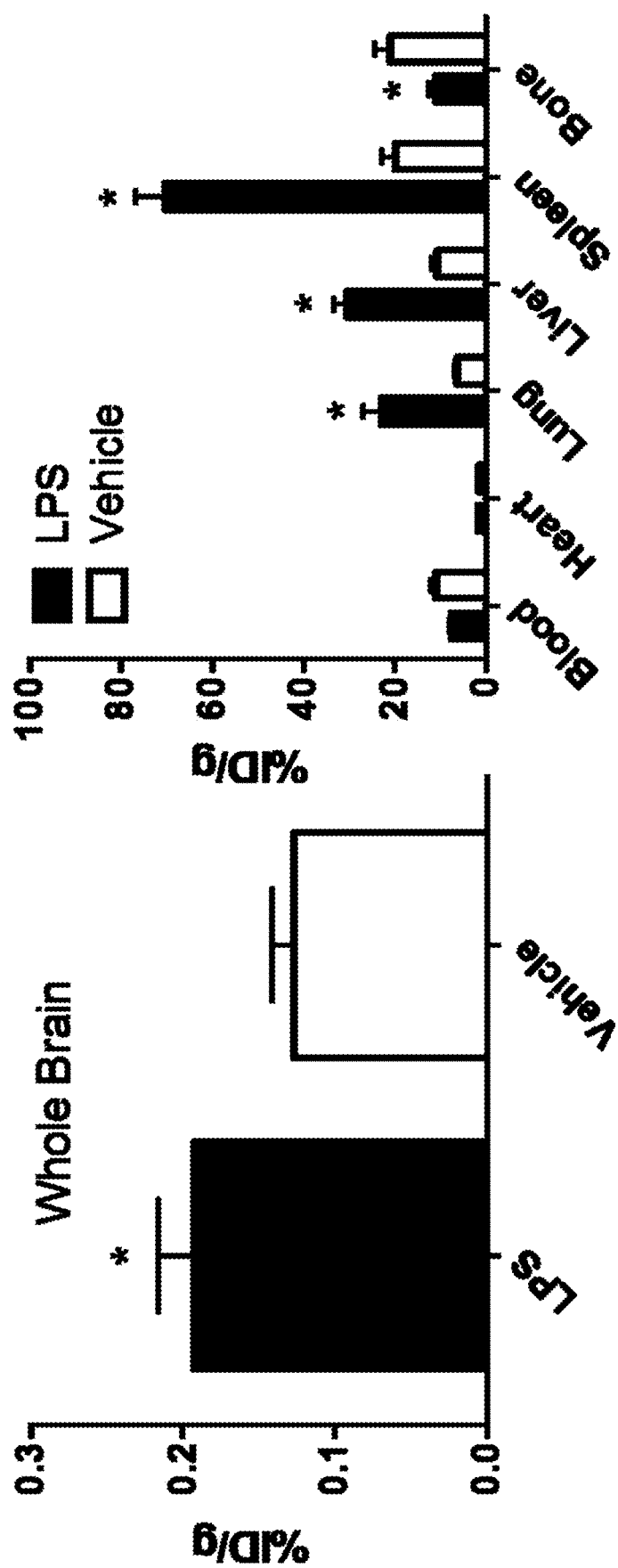
FIG. 11 demonstrates significantly higher uptake of [$^{64}$Cu]TREM1-mAb in brain, lung, liver, and spleen of mice with LPS-induced sepsis. Results are from ex vivo gamma counting of tissues 24 h after mice received i.p. injection of LPS (5 mg/kg) or vehicle, n=6-8 per group.

Results: FIGS. 5, 6, and 7 show PET/CT images and quantitation of the brain images and the respective uptake of TREM-1 in each brain hemisphere. PET/CT imaging results show high [$^{64}$Cu]TREM-1-PET signal in the ischemic brain region of mice with established cerebral infarction (2.64±0.31% ID/g, n=9) compared to the corresponding contralateral (healthy) brain regions (1.79±0.14% ID/g) at early stages of cerebral ischemia (i.e., 1.5-2 days post-stroke). There was negligible, if any, [$^{64}$Cu]TREM-1 PET signal in the brain of sham-operated mice (n=9). To verify the penetration of our TREM-1-PET tracer into the brain, we perfused each mouse with saline after imaging, to remove possible unbound intravascular [$^{64}$Cu]TREM-1, and then harvested brain tissue for ex vivo gamma counting. These results revealed a 1.97-fold higher accumulation of our TREM-1-PET tracer in the left (ischemic) hemisphere compared to the right side, and no difference between brain hemispheres of sham mice (MCAo=1.97±0.25, n=10; Sham =0.98±0.13, n=9). Since these results were comparable to our PET image quantitation, we believe [$^{64}$Cu]TREM-1 is able to sufficiently penetrate the brain of MCAO mice at this time point. Taken together, these results indicate that [$^{64}$Cu] TREM-1 is a promising PET imaging probe that can detect regions containing neuroinflammation with high sensitivity and specificity.

Example 1-3 References

1. Lyman M, Lloyd D G, Ji X, Vizcaychipi M P, Ma D. Neuroinflammation: The role and consequences. Neurosci Res. 2014; 79(1):1-12. PMID: 24144733.
2. Wyss-Coray T, Mucke L. Inflammation in neurodegenerative disease—a double-edged sword. Neuron. 2002; 35:419-32. PMID: 12165466.
3. Jacobs A H, Tavitian B. Noninvasive molecular imaging of neuroinflammation. J Cereb Blood Flow Metab. 2012; 32(7):1393-415. PMID: 22549622.
4. Luus C, Hanani R, Reynolds A, Kassiou M. The development of PET radioligands for imaging the translocator protein (18 kDa): What have we learned? J Label Compd Radiopharm. 2010; 53(7):501-10.
5. Chen M K, Guilarte T R. Translocator protein 18 kDa (TSPO): Molecular sensor of brain injury and repair. Pharmacology and Therapeutics. 2008; 118(1):1-17. PMID: 18374421.
6. Owen D R, Yeo A J, Gunn R N, Song K, Wadsworth G, Lewis A, Rhodes C, Pulford D J, Bennacef I, Parker C A, StJean P L, Cardon L R, Mooser V E, Matthews P M, Rabiner E A, Rubio J P. An 18-kDa translocator protein (TSPO) polymorphism explains differences in binding affinity of the PET radioligand PBR28. J Cereb Blood Flow Metab. 2012; 32(1):1-5. PMID: 22008728.
7. Gibot S, Kolopp-Sarda M N, Berle M C, Cravoisy A, Levy B, Faure G C, Bollaert P E. Plasma level of a triggering receptor expressed on myeloid cells-1: Its diagnostic accuracy in patients with suspectedsepsis. Ann Intern Med. 2004; 141(1):9-15. PMID: 15238365.
8. Knapp S, Gibot S, de Vos A, Versteeg H H, Colonna M, van der Poll T. Cutting edge: expression patterns of surface and soluble triggering receptor expressed on myeloid cells-1 in human endotoxemia. J Immunol. 2004; 173(12):7131-4. PMID: 15585833.
9. Schenk M, Bouchon A, Seibold F, Mueller C. TREM-1-expressing intestinal macrophages crucially amplify chronic inflammation in experimental colitis and inflammatory bowel diseases. J Clin Invest. 2007; 117(10): 3097-106. PMID: 17853946.
10. Yasuda T, Takeyama Y, Ueda T, Shinzeki M, Sawa H, Takahiro N, Kamei K, Ku Y, Kuroda Y, Ohyanagi H. Increased levels of soluble triggering receptor expressed on myeloid cells-1 in patients with acute pancreatitis. Crit Care Med. 2008; 36(7):2048-53. PMID: 18552693.
11. Park J J, Cheon J H, Kim B Y, Kim D H, Kim E S, Kim T II, Lee K R, Kim W H. Correlation of serum-soluble triggering receptor expressed on myeloid cells-1 with clinical disease activity in inflammatory bowel disease. Dig Dis Sci. 2009; 54(7):1525-31. PMID: 18975078.
12. Collins C E, La D T, Yang H-T, Massin F, Gibot S, Faure G, Stohl W. Elevated synovial expression of triggering receptor expressed on myeloid cells 1 in patients with septic arthritis or rheumatoid arthritis. Ann Rheum Dis. 2009; 68(11):1768-74. PMID: 19054829.

13. Ho C-C, Liao W-Y, Wang C-Y, Lu Y-H, Huang H-Y, Chen H-YH-W, Chan W-K, Chen H-YH-W, Yang PC. TREM-1 expression in tumor-associated macrophages and clinical outcome in lung cancer. Am J Respir Crit Care Med. 2008; 177(7):763-70. PMID: 18096709.
14. Weber B, Schuster S, Zysset D, Rihs S, Dickgreber N, Schürch C, Riether C, Siegrist M, Schneider C, Pawelski H, Gurzeler U, Ziltener P, Genitsch V, Tacchini-Cottier F, Ochsenbein A, Hofstetter W, Kopf M, Kaufmann T, Oxenius A, Reith W, Saurer L, Mueller C. TREM-1 deficiency can attenuate disease severity without affecting pathogen clearance. PLoS Pathog. 2014; 10(1):e1003900. PMID: 24453980.
15. Johansson J U, Woodling N S, Wang Q, Panchal M, Liang X, Trueba-Saiz A, Brown H D, Mhatre S D, Loui T, Andreasson K I. Prostaglandin signaling suppresses beneficial microglial function in Alzheimer's disease models. J Clin Invest. 2014; 125(1):350-64. PMID: 25485684.
16. Wu A M. Antibodies and antimatter: The resurgence of immuno-PET. J Nucl Med. 2009; 50(1):2-5. PMID: 19091888.
17. Knowles S M, Wu A M. Advances in immuno-positron emission tomography: Antibodies for molecular imaging in oncology. J Clin Oncol. 2012; 30(31):3884-92. PMID: 22987087.
18. Klohs J, Gräfe M, Graf K, Steinbrink J, Dietrich T, Stibenz D, Bahmani P, Kronenberg G, Harms C, Endres M, Lindauer U, Greger K, Stelzer E H K, Dirnagl U, Wunder A. In vivo imaging of the inflammatory receptor CD40 after cerebral ischemia using a fluorescent antibody. Stroke. 2008; 39(10):2845-52. PMID: 18635859.
19. Blankenberg F G, Kalinyak J, Liu L, Koike M, Cheng D, Goris ML, Green A, Vanderheyden J L, Tong D C, Yenari M A. 99mTc-HYNIC-annexin V SPECT imaging of acute stroke and its response to neuroprotective therapy with anti-Fas ligand antibody. Eur J Nucl Med Mol Imaging. 2006; 33(5):566-74. PMID: 16477433.
20. Arbit E, Cheung N K, Yeh S D, Daghighian F, Zhang J J, Cordon-Cardo C, Pentlow K, Canete A, Finn R, Larson S M. Quantitative studies of monoclonal antibody targeting to disialoganglioside GD2 in human brain tumors. Eur J Nucl Med. 1995; 22(5):419-26. PMID: 7641750.
21. Van de Watering F C J, Rijpkema M, Perk L, Brinkmann U, Oyen W J G, Boerman O C. Zirconium-89 labeled antibodies: A new tool for molecular imaging in cancer patients. Biomed Res Int. 2014; 2014:e203601. PMID: 2499539.
22. Schilling M, Besselmann M, Leonhard C, Mueller M, Ringelstein E B, Kiefer R. Microglial activation precedes and predominates over macrophage infiltration in transient focal cerebral ischemia: a study in green fluorescent protein transgenic bone marrow chimeric mice. Exp Neurol. 2003; 183(1):25-33. PMID:12957485.
23. Martin A, Szczupak B, Gomez-Vallejo V, Domercq M, Cano A, Padro D, Munoz C, Higuchi M, Matute C, Llop J. In vivo PET imaging of the α4β2 nicotinic acetylcholine receptor as a marker for brain inflammation after cerebral ischemia. J Neurosci. 2015; 35(15):5998-6009. PMID: 25878273.
24. Boutin H, Murray K, Pradillo J, Maroy R, Smigova A, Gerhard A, Jones P a., Trigg W. 18F-GE-180: A novel TSPO radiotracer compared to 11C-R-PK11195 in a preclinical model of stroke. Eur J Nucl Med Mol Imaging. 2014; 42(3):503-11. PMID: 25351507.
25. Lartey FM, Ahn G O, Shen B, Cord K T, Smith T, Chua J Y, Rosenblum S, Liu H, James M L, Chernikova S, Lee S W, Pisani L J, Tirouvanziam R, Chen J W, Palmer T D, Chin F T, Guzman R, Graves E E, Loo Jr. B W. PET imaging of stroke-induced neuroinflammation in mice using [18F]PBR06. Mol Imaging Biol. 2014; 16:109-17. PMID: 23836504.
26. Wang Y, Yue X, Kiesewetter D O, Wang Z, Lu J, Niu G, Teng G, Chen X. [(18)F]DPA-714 PET imaging of AMD3100 treatment in a mouse model of stroke. Mol Pharm. 2014; 11(10):3463-70. PMID: 25157648.
27. Strbian D, Durukan a, Pitkonen M, Marinkovic I, Tatlisumak E, Pedrono E, Abo-Ramadan U, Tatlisumak T. The blood-brain barrier is continuously open for several weeks following transient focal cerebral ischemia. Neuroscience. 2008; 153(1):175-81. PMID:18367342.
28. Krueger M, Bechmann I, Immig K, Reichenbach A, Hartig W, Michalski D. Blood-brain barrier breakdown involves four distinct stages of vascular damage in various models of experimental focal cerebral ischemia. J Cereb Blood Flow Metab. 2015; 35(2):292-303. PMID: 25425076.
29. Murakami Y, Akahoshi T, Hayashi I, Endo H, Kawai S, Inoue M, Kondo H, Kitasato H. Induction of triggering receptor expressed on myeloid cells 1 in murine resident peritoneal macrophages by monosodium urate monohydrate crystals. Arthritis Rheum. 2006; 54(2):455-62. PMID: 16447220.
30. Gibot S, Cravoisy A. Soluble form of the triggering receptor expressed on myeloid cells-1 as a marker of microbial infection. Clin Med Res. 2004; 2(3):181-7. PMID: 15931355.
31. Lagler H, Sharif O, Haslinger I, Matt U, Stich K, Furtner T, Doninger B, Schmid K, Gattringer R, de Vos a. F, Knapp S. TREM-1 activation alters the dynamics of pulmonary IRAK-M expression in vivo and improves host defense during pneumococcal pneumonia. J Immunol. 2009; 183(3):2027-36. PMID: 19596984.
32. Cooper M S, Ma M T, Sunassee K, Shaw K P, Williams J D, Paul R L, Donnelly P S, Blower P J. Comparison of 64cu-complexing bifunctional chelators for radioimmunoconjugation: Labeling efficiency, specific activity, and in vitro/in vivo stability. Bioconjug Chem. 2012; 23(5): 1029-39. PMID: 22471317.
33. Ilovich O, Natarajan A, Hori S, Sathirachinda A, Kimura R, Srinivasan A, Gebauer M, Kruip J, Focken I, Lange C, Carrez C, Sassoon I, Blanc V, Sarkar S K, Gambhir S S. Development and validation companion diagnostic agent for antibody-drug conjugate therapy to target the CA6. Radiology. 2015; 276(1):191-8. PMID: 25734548.
34. Konishi S, Hamacher K, Vallabhajosula S, Kothari P, Bastidas D, Bander N, Goldsmith S. Determination of immunoreactive fraction of radiolabeled monoclonal antibodies: What is an appropriate method? Cancer Biother Radiopharm. 2004; 19(6):706-15. PMID: 15665617.
35. Zeng H, Ornatowska M, Joo M S, Sadikot R T. TREM-1 expression in macrophages is regulated at transcriptional level by NFκB and PU.1. Eur J Immunol. 2007; 37(8): 2300-8. PMID: 17634956.
36. Chen L C, Laskin J D, Gordon M K, Laskin D L. Regulation of TREM expression in hepatic macrophages and endothelial cells during acute endotoxemia. Exp Mol Pathol. 2008; 84(2):145-55. PMID: 18222421.
37. McCullough L, Wu L, Haughey N, Liang X, Hand T, Wang Q, Breyer RM, Andreasson K. Neuroprotective function of the PGE2 EP2 receptor in cerebral ischemia. J Neurosci. 2004; 24(1):257-68. PMID: 14715958.
38. Liang X, Lin L, Woodling N S, Wang Q, Anacker C, Pan T, Merchant M, Andreasson K. Signaling via the prostaglandin E2 receptor EP4 exerts neuronal and vascular protection in a mouse model of cerebral ischemia. J Clin Invest. 2011; 121(11):4362-71.PMID: 21965326.
39. Li J, Liang X, Wang Q, Breyer R M, McCullough L, Andreasson K. Misoprostol, an anti-ulcer agent and PGE2 receptor agonist, protects against cerebral ischemia. Neurosci Lett. 2008; 438(2):210-5. PMID: 18472336.
40. Liu C H, Huang S, Kim Y R, Rosen B R, Liu P K. Forebrain ischemia-reperfusion simulating cardiac arrest in mice induces edema and DNA fragmentation in the brain. Mol Imaging. 2007; 6(3):156-70. PMID: 17532882.
41. James M L, Fulton R R, Vercoullie J, Henderson D J. DPA-714, a new translocator protein-specific ligand: Synthesis, radiofluorination, and pharmacologic characterization. J Nucl Med. 2008; 49(5):814- 22. PMID: 18413395.
42. James M L, Belichenko N P, Nguyen T-V V., Andrews L A, Ding Z, Liu H, Bodapati D, Arksey N, Shen B, Cheng Z, Wyss-Coray T, Gambhir S S, Longo F M, Chin F T. PET imaging of translocator protein (18 kDa) in a mouse model of Alzheimer's disease using N-(2,5-Dimethoxybenzyl)-2-18F-Fluoro-N-(2-Phenoxyphenyl)Acetamide. J Nucl Med. 2015; 56(2):311-6. PMID: 25613536.

Example 4

Materials and Methods

DOTA conjugation. Conjugation of anti-mouse anti-TREM mAb (which can be purchased from R&D Systems) with 1,4,7,10-tetraazacyclododecane-1,4,7,10-tetraacetic acid (DOTA) was performed according to standard published procedures using metal-free buffers (1,2). Briefly, a solution of DOTA-NHS ester (Macrocyclics Inc.) in dimethyl sulfoxide (25 mmol/L; 9-12 µL) was added to 1mL of HEPES buffer (0.1 mol/L, pH 8.8) containing 500 µg of TREM-1-mAb, and the reaction mixture was incubated at 4° C. overnight. The reaction was quenched with Tris (Sigma), excess DOTA-NHS was removed by Zeba Spin Desalting Columns (0.5 mL, 50K MWCO, ThermoFisher Scientific), and the resulting solution was buffer-exchanged into ammonium acetate buffer (0.1 M, pH 5.5) for 64Cu labeling. DOTA-conjugate solutions were concentrated by ultrafiltration (Vivaspin 2 mL, Sartorius) to 2-5 mg/mL, snap frozen in liquid nitrogen, and stored at −80° C. prior to radiolabeling. The number of DOTA chelators coupled per TREM-1 was estimated to be 1.5-3.2, via matrix-assisted laser desorption/ionization (MALDI) mass spectrometry.

Radiolabeling. DOTA-TREM-1-mAb was radiolabeled with $^{64}$Cu ($t_{1/2}$=12.7 h) using standard methods and metal-free buffers, with some modifications (1,2). In brief, DOTA-TREM-1-mAb (100 µg) in 50 µL of 0.25 mol/L ammonium acetate buffer (0.1 M, pH 5.5) was mixed with pH-balanced $^{64}$CuCl$_2$ solution (44-74 MBq, pH 5.0-5.5, University of Wisconsin, Madison) at 37° C. with gentle shaking at 300 rpm. After a 60-minute incubation period, 0.1 M EDTA (0.5 M, pH 8.0) was added to a final concentration of 0.01 M and incubated at room temperature for 15 min to scavenge unchelated $^{64}$CuCl$_2$ in the reaction mixture. Purification of $^{64}$Cu-DOTA-TREM-1-mAb was achieved by G25 Sephadex size-exclusion purification (NAP-5 column). Radiochemical purity was determined by instant thin-layer chromatography with TEC-Control Chromatography strips (Biodex Medical Systems, Shirley, NY), developed in saline, and size-exclusion liquid chromatography with a Phenomenex SEC 3000 column (Torrance, CA, USA) with sodium phosophate buffer [0.1 mol/L, pH 6.8)] at a flow rate of 1.0 mL/min. $^{64}$Cu-labeled anti-TREM1 mAb (i.e., [$^{64}$Cu]TREM1-mAb) was obtained with high specific radioactivity (>75 GBq/µmol), radiochemical purity (>99%), and labeling efficiency (70-95%), and formulated in phosphate-buffered saline [0.1 mol/L NaCl, 0.05 mol/L sodium phosphate (pH 7.4)].

In vitro cell uptake studies with HEK293 cells. The uptake of [$^{64}$Cu]TREM1-mAb in HEK293 cells transfected with TREM1 was compared to uptake in untransfected cells, in 24-well plates. One day after transfection, fresh, pre-warmed DMEM containing 0.925 MBq of [$^{11}$C]DASA-23 was added to individual wells (1 mL/well; 9.25±4.63 µmol). Cells were incubated with [$^{64}$Cu]TREM1-mAb at 37 ° C. and 5% CO$_2$ over a 60 and 120 min time course. At the respective time points, plates were placed on ice, washed 3 times with phosphate-buffered saline (PBS), and lysed RIPA buffer (500 µL). 150 µL cell lysates were transferred to counting tubes and decay-corrected radioactivity was determined on a γ counter (Cobra II Auto-Gamma counter; Packard Biosciences Co.). The remaining lysate was frozen and used following radioactive decay for protein determination using a bicinchoninic acid (BCA) 96-well plate assay (Thermo Fisher Scientific Inc.) In addition, 100 µL standards from the 0.925 MBq/mL solution added to cells were counted to quantitate percentage radiotracer uptake.

In vitro cell uptake studies using an immortalized murine microglial cell line. BV2 cells were incubated with either [$^{64}$Cu]TREM1-mAb (n=4 wells) or [$^{64}$Cu]-Isotype-control-mAb (n=4 wells) at 37° C. and 5% CO$_2$ for 120 minutes. A sub-set of cells (n=4 separate wells for each tracer) were pre-treated with 100-fold unconjugated TREM1-mAb (compared to mass amount associated with the tracer dose per well) for 30 min prior to adding radiotracer to serve as a blocking study to evaluate specificity of tracer binding. After incubating cells with each tracer for 120 min, plates were washed 3 times with phosphate-buffered saline (PBS), and lysed RIPA buffer (500 µL). 150 µL cell lysates were transferred to counting tubes and decay-corrected radioactivity was determined on a y counter (Cobra II Auto-Gamma counter; Packard Biosciences Co.). In addition, 50 µL standards from the radiotracer stock media solution added to cells were counted to quantitate percentage radiotracer uptake. After samples were counted, a bicinchoninic acid (BCA) 96-well plate assay (Thermo Fisher Scientific Inc.) was used to determine the amount of protein within each sample. The radioactive signal was later normalized to the amount of protein within each sample.

LPS-induced sepsis in C57BL/6 mice. Lipopolysaccharide (LPS) from Escherichia coli lyophilized powder (Sigma) was dissolved in sterile saline immediately prior to injecting C57BL/6 female mice (8-12 weeks) intraperitoneally (i.p.) at a concentration of 5 mg/kg. Vehicle mice received the same volumes of sterile saline (according to their weight).

PET/CT imaging of LPS and vehicle mice. LPS and vehicle mice were injected with [$^{64}$Cu]TREM1-mAb (1.59±0.09 MBq) intravenously (i.v.). Mice were then imaged at 3 hours and 24 hours post i.v. injection. Mice were anesthetized using isoflurane gas (2.0-3.0% for induction and 1.5-2.5% for maintenance). A CT image was acquired just before each PET scan to provide an anatomic reference frame for the respective PET data. CT raw images were acquired at 80 kVp at 500 µA, two bed position, half-scan 220° of rotation, and 120 projections per bed position with a cone beam micro-X-ray source (50 µm focal spot size) and a 2048×3072 pixel X-ray detector. On the basis of attenuation correction from the CT measurements, each 10-minute static PET scan was acquired with default settings of coincidence, a timing window of 3.4 ns, and an energy window of 350 to 650 keV. PET and CT Image files were co-registered and analyzed with Inveon Research Workspace software (IRW, version 4.0; Siemens).

Biodistribution. After the final PET scan, mice were deeply anesthetized with 2-2.5% isoflurane, and blood samples (100-200 μL) were collected via cardiac puncture immediately prior to transcardial perfusion with 20 mL of PBS. Following perfusion, the heart, lungs, liver, spleen, kidney, small intestine, bone (femur) and muscle were dissected from each mouse, placed in a tube for gamma counting, and weighed; satisfactory perfusions were verified by visual inspection of brain tissue. Tissue-associated radioactivity in each dissected organ was assessed via an automated gamma counter (Cobra II Auto-Gamma counter; Packard Biosciences Co.), normalized to tissue weight and to amount of radioactivity administered to each mouse, and decay-corrected to time of tracer injection using diluted aliquots of the initial administered dose as standards.

Image analysis. Regions of interest (ROIs) were drawn around the spleen, liver, and bone (femur) using Inveon Research Workspace (IRW, version 4.0; Siemens). These ROIs were then normalized to the amount of radioactivity administered to each mouse and decay-corrected to the time of scanning.

Results

After labeling DOTA-TREM-mAb with $^{64}$Cu we assessed the in vitro binding affinity, specificity, and immunoreactivity of this new PET tracer using standard protocols in HEK293 cells +/− TREM transfection and in murine microglia +/− LPS treatment. In studies using HEK293 cells, [$^{64}$Cu]TREM1-mAb displayed 24-fold higher binding in transfected versus untransfected cells (FIG. 1) (0.556±0.002 vs 0.002±0.0002, p<0.001, n=4 replicates), confirming in vitro its high specificity for TREM1. Blocking studies with unlabeled anti-TREM1 mAb led to a significant reduction of [$^{64}$Cu]TREM1-mAb binding in transfected cells (0.556±0.002 vs. 0.017±0.001, p<0.001, n=4 replicates), further corroborating the specificity of our new PET tracer.

In vitro cell studies using BV2 cells, an immortalized murine microglial cell line, showed [$^{64}$Cu]TREM1-mAb binds specifically to TREM1 in these cells, as demonstrated by the significantly higher uptake of this tracer in BV2 cells compared to those pre-treated for 30 min with unconjugated-TREM1-mAb (100-fold dose of PET tracer). [$^{64}$Cu]TREM1-mAb displayed 2.4 higher binding in BV2 cells compared to blocked BV2 cells (0.00045±2.99×10$^{-5}$ vs. 0.00019±2.03×10$^{-5}$, p<0.001, n=4 replicates). BV2 cells incubated with [$^{64}$Cu]Isotype-Control PET tracer showed significantly lower uptake than BV2 cells incubated with [$^{64}$Cu]TREM1-mAb (0.000454±2.99×10$^{-5}$ vs. 0.000253±0.0001, p<0.001, n=4 replicates). The uptake of [$^{64}$Cu]isotype-control PET tracer in BV2 cells was comparable to [$^{64}$Cu]TREM1-mAb uptake in BV2 cells that had been pre-blocked, further confirming that the high uptake we observed with [$^{64}$Cu]TREM1-mAb in BV2 cells is due to specific binding to TREM1.

Furthermore, the uptake among [$^{64}$Cu]Isotype-Control PET tracer was comparable to uptake in cells that had been pre-blocked, further confirming that the high uptake we observed with [$^{64}$Cu]TREM1-mAb in BV2 cells is due to specific binding to TREM1.

Following in vitro studies, we performed in vivo PET imaging and ex vivo biodistribution studies with [$^{64}$Cu]TREM1-mAb in a mouse model of LPS-induced sepsis. These studies involved intravenous administration of [$^{64}$Cu]TREM1-mAb (90-100 μCi) immediately after intraperitoneal (i.p.) injection of either LPS (5 mg/kg) or vehicle. After 24 h of allowing the tracer to circulate and bind TREM1 in vivo, mice underwent a 10 min static PET/CT image and were then deeply anesthetized, perfused with saline to remove possible unbound intravascular [$^{64}$Cu]TREM1-mAb, and organs were harvested for gamma counting to determine percentage injected dose per gram (%ID/g) of [$^{64}$Cu]TREM1-mAb bound in these tissues.

In vivo PET imaging results (FIG. 2) demonstrated markedly higher levels of [$^{64}$Cu]TREM1-mAb uptake in spleen, liver, and lungs compared to vehicle-treated mice. This pattern of TREM1 PET tracer uptake fits with the known increase in splenic myeloid cells that occurs after LPS challenge, and since lung and liver are among the first organs to be affected/inflamed in sepsis. Interestingly, we observed lower TREM1 PET tracer uptake in bones of mice with LPS-induced sepsis compared to vehicle-treated mice, possibly highlighting the mobilization of TREM1-positive myeloid cells from bone marrow to affected organs.

Figure 3:
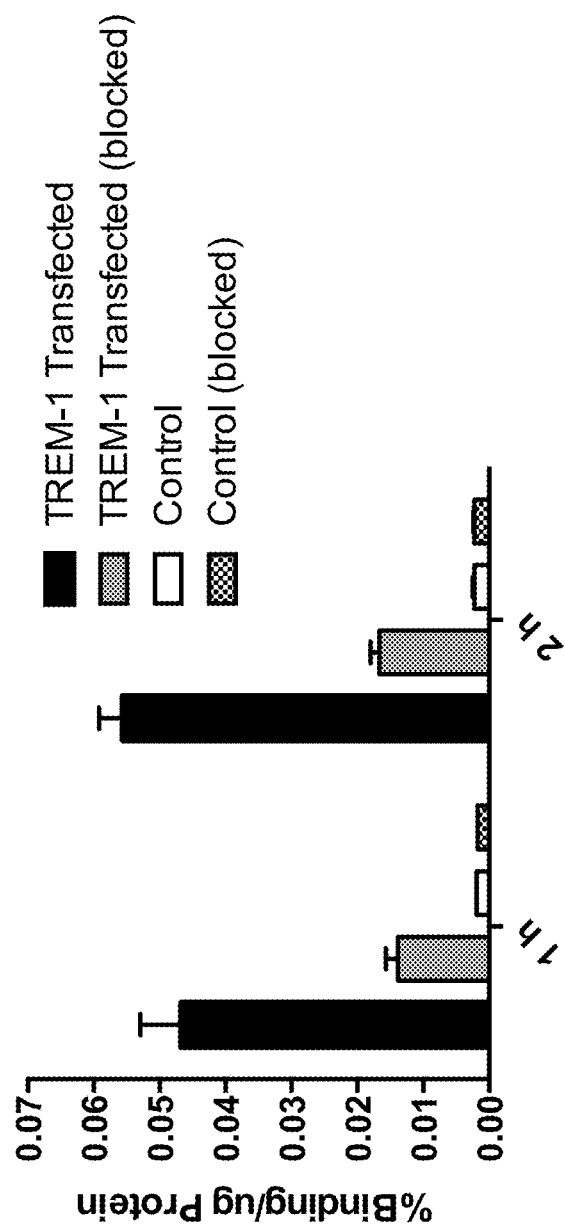
FIG. 3 shows the results of [$^{64}Cu$]TREM-1 cell binding studies.

Quantitation of PET images (FIG. 3) acquired 24 h after mice received i.p. injection of LPS (5 mg/kg) or saline alone revealed significantly higher uptake of [$^{64}$Cu]TREM1-mAb in spleen and liver of LPS-treated (n=8) compared to vehicle-treated mice (n=5) and LPS mice that were instead injected with a radiolabeled isotype control PET tracer (n=3). LPS mice injected with radiolabeled isotype control mAb had significantly lower uptake in spleen and bone marrow compared to LPS mice injected with [$^{64}$Cu]TREM1-mAb.

Ex vivo biodistribution results (FIG. 4) reveal significantly higher uptake of [$^{64}$Cu]TREM1-mAb in brain, lung, liver, and spleen of mice with LPS-induced sepsis, as per gamma counting of tissues 24 h after mice received i.p. injection of LPS (5 mg/kg) or vehicle, n=3 per group. Importantly, we also observed 1.5-fold higher brain uptake of [$^{64}$Cu]TREM1-mAb in LPS-injected mice (0.19±0.02 vs. 0.13±0.01% ID/g, p<0.05, n=3).

Example 4 References (1) Ilovich O., Natarajan A., Hori S., et al. Development and Validation Companion Diagnostic Agent for Antibody-Drug Conjugate Therapy to Target the CA6. 2015; 276: 191-198. PMID: 25734548
(2) Cooper M S., Ma M T., Sunassee K., et al. Comparison of 64cu-complexing bifunctional chelators for radioimmunoconjugation: Labeling efficiency, specific activity, and in vitro/in vivo stability. Bioconjug Chem. 2012; 23:1029-1039. PMID: 22471317

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, "about 0" can refer to 0, 0.001, 0.01, or 0.1. In an embodiment, the term "about" can include traditional rounding according to significant figures of the numerical value. In addition, the phrase "about 'x' to 'y'" includes "about 'x' to about 'y'".

It should be emphasized that the above-described embodiments of the present disclosure are merely possible examples of implementations, and are set forth only for a clear understanding of the principles of the disclosure. Many variations and modifications may be made to the above-described embodiments of the disclosure without departing substantially from the spirit and principles of the disclosure. All such modifications and variations are intended to be included herein within the scope of this disclosure.

We claim:

1. A method of monitoring the progress of neurological tissue inflammation from a neurological disease in a subject, the method comprising:
    administering to a subject a labeled probe, wherein the labeled probe includes a TREM-1 antibody and a radiolabel, and wherein the radiolabel is selected from $^{64}Cu$, $^{18}F$, and $^{89}Zr$;
    imaging at least a portion of the subject; and
    detecting a signal from the labeled probe, wherein detecting the signal corresponds to detecting the neurological tissue inflammation, wherein the signal is monitored over time.

2. The method of claim 1, wherein the neurological disease is selected from the group consisting of Alzheimer's disease, multiple sclerosis, epilepsy, traumatic brain injury, Huntington's disease, amyotrophic lateral sclerosis, Parkinson's disease, sepsis, stroke, chronic fatigue syndrome, depression, and schizophrenia.

3. The method of claim 1, wherein the detection of the labeled probe is performed in vitro using Positron Emission Tomography (PET), Computerized Tomography (CT), or a combination thereof.

4. The method of claim 1, wherein chelator is (1,4,7,10-tetraazacyclododecane-1,4,7,10-tetraacetic acid).

5. The method of claim 1, wherein chelator is NOTA (1,4,7-Triazacyclononane-1,4,7-triacetic acid).

6. The method of claim 1, wherein chelator is EDTA (Ethylenediaminetetraacetic acid).

7. The method of claim 1, wherein chelator is Df (Desferrioxamine).

8. The method of claim 1, wherein chelator is DTPA (Diethylenetriaminepentaacetic acid).

9. The method of claim 1, wherein chelator is and TETA (Triethylenetetramine).

10. The method of claim 1, wherein the radiolabel is $^{64}Cu$.

11. The method of claim 1, wherein the radiolabel is $^{18}F$.

12. The method of claim 1, wherein the radiolabel is $^{89}Zr$.

* * * * *